(12) United States Patent
Rodgers et al.

(10) Patent No.: US 6,462,037 B1
(45) Date of Patent: Oct. 8, 2002

(54) 1,4-BENZODIAZEPIN-2-ONES USEFUL AS HIV REVERSE TRANSCRIPTASE INHIBITORS

(75) Inventors: James D. Rodgers, Landenberg, PA (US); Barry L. Johnson; Haisheng Wang, both of Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/578,021

(22) Filed: May 25, 2000

Related U.S. Application Data

(60) Provisional application No. 60/135,966, filed on May 26, 1999.

(51) Int. Cl.$^7$ .................. C07D 243/14; C07D 401/06; C07D 405/06; C07D 409/06; A61K 31/5513
(52) U.S. Cl. .............. 514/220; 514/221; 540/497; 540/504; 540/505; 540/507; 540/509
(58) Field of Search .................. 514/220, 221; 540/504, 505, 507, 509, 514, 497

(56) References Cited

U.S. PATENT DOCUMENTS

| | | | |
|---|---|---|---|
| 3,682,892 A | 8/1972 | Ning et al. | 260/239 |
| 3,714,145 A | 1/1973 | Bell et al. | 260/239 |
| 3,801,569 A | 4/1974 | Ning et al. | 260/239 |
| 3,864,330 A | 2/1975 | Katsube et al. | 260/239 |
| 4,021,421 A | 5/1977 | Kisfaludy et al. | 260/239 |
| 4,045,433 A | 8/1977 | Rohricht et al. | 260/239 |
| 4,316,897 A | 2/1982 | Lotz | 424/244 |
| 4,764,512 A | 8/1988 | Molino et al. | 514/183 |
| 4,957,915 A | 9/1990 | Kim et al. | 514/221 |
| 5,175,159 A | 12/1992 | Bock et al. | 514/221 |
| 5,519,021 A | 5/1996 | Young et al. | 514/230.5 |
| 5,532,357 A | 7/1996 | Rodgers et al. | 540/492 |
| 5,550,126 A | 8/1996 | Horwell et al. | 514/237.5 |

FOREIGN PATENT DOCUMENTS

| | | |
|---|---|---|
| DE | 4320347 | 12/1994 |
| EP | 0490590 | 6/1992 |
| EP | 0530994 | 3/1993 |
| EP | 0569083 | 11/1993 |
| EP | 0705607 | 4/1996 |
| EP | 0710725 | 5/1996 |
| GB | 2281297 | 3/1995 |
| WO | 9312791 | 7/1993 |
| WO | 9512583 | 5/1995 |
| WO | 9513273 | 5/1995 |
| WO | 9611940 | 4/1996 |
| WO | 9629329 | 9/1996 |

OTHER PUBLICATIONS

Taylor et al., Synthesis of Some 1H–1,3–Benzodiazepines, Journal of Chem. Soc., Perkin Trans. 1 (1976), (12), 1331–8.

Houpis et al., Synthesis of a New Generation Reverse Transcriptase Inhibitor via the BCl3/GaCl3–Induced Condensation of Anilines With Nitriles (Sugasawa Reaction), Tetr. Lett. 1994, 35 (37), 6811–6814.

Tucker et al., Synthesis of a Series of 4–(Arylethynyl)–6–chloro–4–cyclopropyl–3,4–dihydroquinazolin–2(1H)–ones as Novel Non–Nucleoside HIV–1 Reverse Transcriptase Inhibitors, J. Med Chem. 1994, 37, 2437–2444.

Huffman et al., Lithium Alkoxides of Cinchona Alkaloids as Chiral Controllers for Enantioselective Acetylide Addition to Cyclic N–Acyl Ketimines, J. Org. Chem. 1995, 60, 1590–1594.

T. Prueksaritanont et al, Drug Metabolism and Disposition, Species Differences in the Metabolism of a potent HIV–1 Reverse Transcriptase Inhibitor, vol. 23, No. 7, 1995, 688–95, XP002072027.

M. Yamamoto et al, Chemical and Pharmaceutical Bulletin, Synthetic Studies on Quinazoline Derivatives, vol. 29, No. 8, 1981, 2135–56, XP002080827.

*Primary Examiner*—Bruck Kifle
(74) *Attorney, Agent, or Firm*—Mary K. VanAtten

(57) ABSTRACT

The present invention relates to 1,4-benzodiazepin-2-ones of Formula (I):

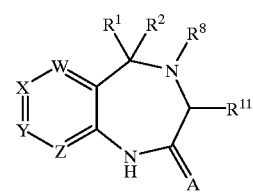

or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

33 Claims, No Drawings

1,4-BENZODIAZEPIN-2-ONES USEFUL AS HIV REVERSE TRANSCRIPTASE INHIBITORS

This application claims priority to U.S. Provisional Application No. 60/135,966 filed May 26, 1999.

FIELD OF THE INVENTION

This invention relates generally to 1,4-benzodiazepin-2-ones and 1,4-benzoxazepin-2-ones which are useful as inhibitors of HIV reverse transcriptase, pharmaceutical compositions and diagnostic kits comprising the same, methods of using the same for treating viral infection or as assay standards or reagents, and intermediates and processes for making the same.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

An active area of research is in the discovery of non-nucleoside HIV reverse transcriptase inhibitors. As an example, it has been found that certain benzoxazinones and quinazolinones are active in the inhibition of HIV reverse transcriptase, the prevention or treatment of infection by HIV and the treatment of AIDS.

U.S. Pat. No. 5,519,021 describe reverse transcriptase inhibitors which are benzoxazinones of the formula:

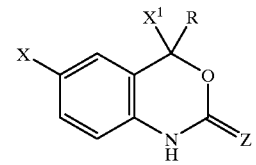

wherein X is a halogen, Z may be O.

EP 0,530,994 and WO 93/04047 describe HIV reverse transcriptase inhibitors which are quinazolinones of the formula A:

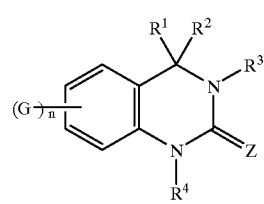

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(−)-6-chloro-4-cyclopropyl-3,4-dihydro-4((2-pyridyl)ethynyl)-2(1H)-quinazolinone.

Synthetic procedures for making quinazolinones like those described above are detailed in the following references: Houpis et al, *Tetr. Lett.* 1994, 35(37), 6811–6814;

Tucker et al, *J. Med. Chem.* 1994, 37, 2437–2444; and, Huffman et al, *J. Org. Chem.* 1995, 60, 1590–1594.

DE 4,320,347 illustrates quinazolinones of the formula:

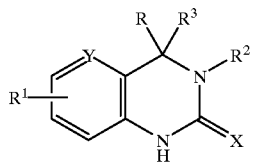

wherein R is a phenyl, carbocyclic ring, or a heterocyclic ring. Compounds of this sort are not considered to be part of the present invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention or a pharmaceutically acceptable salt form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

It is another object of the present invention to provide novel 1,4-benzodiazepin-2-ones for use in therapy.

It is another object of the present invention to provide the use of novel 1,4-benzodiazepin-2-ones for the manufacture of a medicament for the treatment of HIV infection.

These and other objects, which will become apparent during the following detailed description, have been achieved by the inventors' discovery that compounds of formula (I):

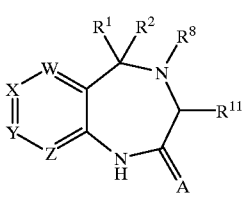

wherein $R^1$, $R^2$, $R^{11}$, A, B, W, X, Y, and Z are defined below, stereoisomeric forms, mixtures of stereoisomeric forms, or pharmaceutically acceptable salt forms thereof, are effective reverse transcriptase inhibitors.

DETAILED DESCRIPTION OF PREFERRED EMBODIMENTS

[1] Thus, in a first embodiment, the present invention provides a novel compound of Formula (I):

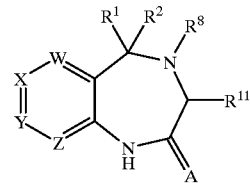

or a stereoisomer or pharmaceutically acceptable salt form thereof, wherein:

A is O or S;

W is N or $CR^3$;

X is N or $CR^{3a}$;

Y is N or $CR^{3b}$;

Z is N or $CR^{3c}$;

provided that if two of W, X, Y, and Z are N, then the remaining are other than N;

$R^1$ is selected from the group cyclopropyl and $C_{1-3}$ alkyl substituted with 0–7 halogen;

$R^2$ is selected from the group H, —$R^{2c}$, —$CH_2C(=O)R^{2c}$, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C=C—R^{2b}$, —$OCHR^{2a}C=R^{2c}$, $OCHR^{2a}C\equiv C—R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C=C—R^{2b}$, —$SCHR^{2a}C=R^{2c}$, —$SCHR^{2a}C\equiv C—R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C=C—R^{2b}$, —$NHCHR^{2a}C=R^{2c}$, and —$NHCHR^{2a}C\equiv C—R^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group $C_{1-6}$ alkyl substituted with 0–2 $R^4$; $C_{2-5}$ alkenyl substituted with 0–2 $R^4$; $C_{2-5}$ alkynyl substituted with 0–1 $R^4$; $C_{3-6}$ cycloalkyl substituted with 0–2 $R^{3d}$; phenyl substituted with 0–2 $R^{3d}$; and 3–6 membered heterocyclic system containing 1–3 heteroatoms selected from the group O, N, and S, substituted with 0–2 $R^{3d}$;

alternatively, the group —$NR^{2a}R^{2c}$ represents a 4–7 membered cyclic amine, wherein 0–1 carbon atoms are replaced by O or $NR^5$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —C(O)$R^6$, —NHC(O)$R^7$, —NHC(O)$NR^5R^{5a}$, —$NHSO_2R^{10}$, —$SO_2NR^5R^{5a}$, and a 5–6 membered heteroaromatic ring containing 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —C(O)$R^6$, —NHC(O)$R^7$, —NHC(O)$NR^5R^{5a}$, —$NHSO_2R^{10}$, —$SO_2NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3a}$ and R$^{3b}$ together form —OCH$_2$O—;

R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^4$ is selected from the group F, Cl, Br, I, CF$_3$, C$_{1-6}$ alkyl substituted with 0–2 R$^{3e}$; C$_{3-10}$ carbocycle substituted with 0–2 R$^{3e}$; phenyl substituted with 0–5 R$^{3e}$; and a 5–10 membered heterocyclic system containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group C$_{1-3}$ alkyl and C$_{1-3}$ alkoxy;

R$^8$ is selected from the group H, OH, C$_{1-6}$ alkyl substituted with 0–2 R$^9$; C$_{2-6}$ alkenyl substituted with 0–2 R$^9$; C$_{2-6}$ alkynyl substituted with 0–2 R$^9$; C$_{3-5}$ cycloalkyl substituted with 0–2 R$^{3f}$; phenyl substituted with 0–5 R$^{3f}$; and a 5–6 membered heterocyclic system containing 1–3 heteroatoms selected from the group O, N, and S, substituted with 0–2 R$^{3f}$;

R$^9$ is selected from the group benzoyl; C$_{3-10}$ carbocycle substituted with 0–5 R$^{3f}$; and a 5–10 membered heterocyclic system containing 1–3 heteroatoms selected from the group O, N, and S, substituted with 0–2 R$^{3f}$;

R$^{10}$ is selected from the group C$_{1-4}$ alkyl and phenyl; and

R$^{11}$ is selected from the group H, C$_{1-6}$ alkyl, C$_{1-6}$ alkenyl, C$_{1-6}$ alkynyl, aralkyl, aryl.

[2] In a preferred embodiment, the present invention provides a novel compound of Formula (I), wherein:

A is O;
W is N or CR$^3$;
X is N or CR$^{3a}$;
Y is N or CR$^{3b}$;
Z is N or CH;
R$^1$ is selected from the group cyclopropyl and C$_{1-3}$ alkyl substituted with 1–7 halogen;
R$^2$ is selected from the group H, —R$^{2c}$, —CH$_2$C(=O) R$^{2c}$, —OR$^{2c}$, —OCHR$^{2a}$R$^{2b}$, —OCH$_2$CHR$^{2a}$R$^{2b}$, —O(CH$_2$)$_2$CHR$^{2a}$R$^{2b}$, —OCHR$^{2a}$C=C—R$^{2b}$, —OCHR$^{2a}$C=R$^{2c}$, and —OCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-5}$ alkyl substituted with 0–2 R$^4$; C$_{2-5}$ alkenyl substituted with 0–2 R$^4$; C$_{2-5}$ alkynyl substituted with 0–1 R$^4$; C$_{3-6}$ cycloalkyl substituted with 0–2 R$^{3d}$; and phenyl substituted with 0–2 R$^{3d}$; R$^3$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

R$^{3a}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O) NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$, at each occurrence, is independently selected from the group H, C$_{1-3}$ alkyl, OH, C$_{1-3}$ alkoxy, F, and Cl;

alternatively, R$^{3a}$ and R$^{3b}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^4$ is selected from the group Cl, F, CF$_3$; C$_{1-4}$ alkyl substituted with 0–2 R$^{3e}$; C$_{3-5}$ carbocycle substituted with 0–2 R$^{3e}$; phenyl substituted with 0–5 R$^{3e}$; and a 5–6 membered heterocyclic system containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, CH(CH$_3$)$_2$, OCH$_3$, OC$_2$H$_5$, and OCH(CH$_3$)$_2$; and, R$^8$ is selected from the group H, OH; C$_{1-6}$ alkyl substituted with 0–2 R$^9$; C$_{2-6}$ alkenyl substituted with 0–2 R$^9$; C$_{2-6}$ alkynyl substituted with 0–2 R$^9$; C$_{3-5}$ cycloalkyl substituted with 0–2 R$^{3f}$; phenyl substituted with 0–5 R$^{3f}$; and a 5–6 membered heterocyclic system containing 1–3 heteroatoms selected from the group O, N, and S, substituted with 0–2 R$^{3f}$;

R$^9$ is selected from the group benzoyl; C$_{3-10}$ carbocycle substituted with 0–5 R$^{3f}$; and a 5–10 membered heterocyclic system containing 1–3 heteroatoms selected from the group O, N, and S, substituted with 0–2 R$^{3f}$;

R$^{11}$ is selected from the group H, cyclopropyl, CH$_3$, C$_2$H$_5$, and CH(CH$_3$)$_2$, n-propyl, n-butyl, iso-butyl.

[3] In a more preferred embodiment, the present invention provides a novel compound of Formula (I), wherein:

A is O;
W is CR$^3$;
X is CR$^{3a}$;
Y is CH;
Z is CH;
R$^1$ is selected from the group CHF$_2$, CF$_3$, and C$_2$F$_5$;
R$^2$ is selected from the group H, —R$^{2c}$, —CH$_2$C(=O)R$^{2c}$, —OCH$_2$R$^{2b}$, —OCH$_2$CH$_2$R$^{2b}$, —OCH$_2$C=C—R$^{2b}$, and —OCH$_2$C≡C—R$^{2b}$;
R$^{2b}$ is H or R$^{2c}$;
R$^{2c}$ is selected from the group C$_{1-4}$ alkyl substituted with 0–2 R$^4$; C$_{2-3}$ alkenyl substituted with 0–2 R$^4$; C$_{2-3}$ alkynyl substituted with 0–1 R$^4$; and C$_{3-6}$ cycloalkyl substituted with 0–2 R$^{3d}$;
R$^3$, at each occurrence, is independently selected from the group H, C$_{1-3}$ alkyl, OH, C$_{1-3}$ alkoxy, F, Cl, Br, NR$^5$R$^{5a}$, NO$_2$, —CN, C(O)R$^6$, NHC(O)R$^7$, and NHC(O)NR$^5$R$^{5a}$;
R$^{3a}$, at each occurrence, is independently selected from the group H, C$_{1-3}$ alkyl, OH, C$_{1-3}$ alkoxy, F, Cl, Br, NR$^5$R$^{5a}$, NO$_2$, —CN, C(O)R$^6$, NHC(O)R$^7$, and NHC(O)NR$^5$R$^{5a}$;
alternatively, R$^3$ and R$^{3a}$ together form —OCH$_2$O—;
R$^{3e}$, at each occurrence, is independently selected from the group H, C$_{1-4}$ alkyl, —OH, C$_{1-4}$ alkoxy, OCF$_3$, F, Cl, —NR$^5$R$^{5a}$, —C(O)R$^6$, and —SO$_2$NR$^5$R$^{5a}$;
R$^{3f}$, at each occurrence, is independently selected from the group H, C$_{1-4}$ alkyl, —OH, C$_{1-4}$ alkoxy, OCF$_3$, F, Cl, —NR$^5$R$^{5a}$, —C(O)R$^6$, and —SO$_2$NR$^5$R$^{5a}$;
R$^4$ is selected from the group Cl, F, CF$_3$, C$_{1-4}$ alkyl substituted with 0–1 R$^{3e}$; C$_{3-5}$ carbocycle substituted with 0–2 R$^{3e}$; phenyl substituted with 0–2 R$^{3e}$; and a 5–6 membered heterocyclic system containing 1–3 heteroatoms selected from the group O, N, and S, substituted with 0–1 R$^{3e}$;
R$^5$ and R$^{5a}$ are independently selected from the group H, CH$_3$ and C$_2$H$_5$;
R$^6$ is selected from the group H, OH, CH$_3$, C$_2$H$_5$, OCH$_3$, OC$_2$H$_5$, and NR$^5$R$^{5a}$;
R$^7$ is selected from the group CH$_3$, C$_2$H$_5$, OCH$_3$, and OC$_2$H$_5$; and,
R$^8$ is selected from the group H, OH; C$_{1-6}$ alkyl substituted with 0–2 R$^9$; C$_{2-6}$ alkenyl substituted with 0–2 R$^9$; C$_{2-6}$ alkynyl substituted with 0–2 R$^9$; C$_{3-5}$ cycloalkyl substituted with 0–2 R$^{3f}$; phenyl substituted with 0–5 R$^{3f}$; and a 5–6 membered heterocyclic system containing 1–3 heteroatoms selected from the group O, N, and S, substituted with 0–2 R$^{3f}$;
R$^9$ is selected from the group benzoyl; C$_{3-6}$ carbocycle substituted with 0–5 R$^{3f}$; and a 5–6 membered heterocyclic system containing 1–3 heteroatoms selected from the group O, N, and S, substituted with 0–2 R$^{3f}$;
R$^{11}$ is selected from the group H, cyclopropyl, CH$_3$, C$_2$H$_5$, and CH(CH$_3$)$_2$, n-propyl, n-butyl, iso-butyl.

[4] In an even more preferred embodiment, the present invention provides a novel compound of Formula (I), wherein:
A is O;
W is CR$^3$;
X is CR$^{3a}$;
Y is CH;
Z is CH;
R$^1$ is CF$_3$;
R$^2$ is selected from the group H, —R$^{2c}$, and —CH$_2$C(=O)R$^{2c}$;
R$^{2c}$ is selected from the group C$_{1-4}$ alkyl substituted with 1 R$^4$; C$_{2-3}$ alkenyl substituted with 1 R$^4$; and C$_{2-3}$ alkynyl substituted with 1 R$^4$;
R$^3$, at each occurrence, is independently selected from the group H, methyl, ethyl, OH, methoxy, ethoxy, F, and Cl;
R$^{3a}$, at each occurrence, is independently selected from the group H, methyl, ethyl, OH, methoxy, ethoxy, F, and Cl;
alternatively, R$^3$ and R$^{3a}$ together form —OCH$_2$O—;
R$^{3e}$, at each occurrence, is independently selected from the group H, methyl, ethyl, OH, methoxy, ethoxy, F, and Cl;
R$^{3f}$, at each occurrence, is independently selected from the group H, methyl, ethyl, OH, methoxy, ethoxy, F, and Cl;
R$^4$ is selected from the group Cl, F, CF$_3$, CH$_3$, CH$_2$CH$_3$, CH(CH$_3$)$_2$; cyclopropyl-substituted with 0–1 R$^{3e}$; 1-methyl-cyclopropyl-substituted with 0–1 R$^{3e}$; cyclobutyl substituted with 0–1 R$^{3e}$; phenyl substituted with 0–2 R$^{3e}$; and a 5–6 membered heterocyclic system containing 1–3 heteroatoms selected from the group O, N, and S, substituted with 0–1 R$^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;
R$^5$ and R$^{5a}$ are independently selected from the group H, CH$_3$ and C$_2$H$_5$;
R$^8$ is selected from the group H, OH; C$_{1-6}$ alkyl substituted with 0–1 R$^9$; C$_{2-6}$ alkenyl substituted with 0–1 R$^9$; C$_{2-6}$ alkynyl substituted with 0–1 R$^9$; C$_{3-5}$ cycloalkyl substituted with 0–2 R$^{3f}$; and phenyl substituted with 0–5 R$^{3f}$;
R$^9$ is selected from the group benzoyl; C$_{3-6}$ cycloalkyl substituted with 0–3 R$^{3f}$; and a C$_{3-6}$ phenyl substituted with 0–3 R$^{3f}$; and a 5–6 membered heterocyclic system containing 1–3 heteroatoms selected from the group O, N, and S, substituted with 0–2 R$^{3f}$; wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl; and
R$^{11}$ is selected from the group H, cyclopropyl, CH$_3$, C$_2$H$_5$, and CH(CH$_3$)$_2$, n-propyl, n-butyl, iso-butyl.

[5] In a further preferred embodiment the present invention provides compound of wherein:
A is O;
W is CR$^3$;
X is CR$^{3a}$;
Y is CH;
Z is CH;
R$^1$ is CF$_3$;
R$^3$ is H, F, Cl, methyl, or methoxy;
R$^{3a}$ is H, F, Cl, methyl, or methoxy;
R$^2$ is H, methyl-, ethyl-, propyl-, butyl-, pentyl-, hexyl-, CF$_3$CH$_2$CH$_2$—, CF$_3$CH$_2$CH$_2$CH$_2$—, PhCH$_2$—, PhCH$_2$CH$_2$—, cycPr—CH$_2$—, cycPr—CH$_2$CH$_2$—, pyrid-2-yl-CH$_2$—, cycPr—C(=O)CH$_2$—, cycPr—CH=CH—, iPr—C≡C—, cycPr—C≡C—, or thien-2-yl-C≡C—;

R[8] is H, OH, methyl, ethyl, n-propyl, i-propyl, n-butyl, n-hexyl, n-pentyl, 3-CH₃-pentyl, (CH₃)₂CHCH₂CH₂—, —CH₂CH=C(CH₃)₂, —CH₂CH₂CH₂CH=CH₂, —CH₂CH=CHC₂H₅, —CH₂C≡CH, —CH₂C≡CCH₃, —CH₂C≡C—cycPr, —CH₂C≡C—CH₂CH₂CH₃, —CH₂C≡CCH₂CH₃, —CH₂C≡C-isopropyl, —CH₂C≡C-phenyl, -phenyl, —CH₂CH₂-phenyl, —CH₂CH₂CH₂-phenyl, —CH₂(2-F-6-CH₃-phenyl), —CH₂CH₂(2-Cl-phenyl), —CH₂CH₂(2-I-phenyl), —CH₂CH₂(3-Cl-phenyl), benzyl-, 2-CH₃-benzyl-, 2-F-benzyl-, 2-Cl-benzyl-, 2-Br-benzyl-, 2-MeO-benzyl-, 2-CN-benzyl-, 3-F-benzyl-, 3-Cl-benzyl-, 3-MeO-benzyl-, 3-CN-benzyl-, 2,3-diF-benzyl-, 2,4-diF-benzyl-, 2,5-diF-benzyl-, 2,6-diF-benzyl-, 2,6-diCl-benzyl-, 2-Cl-6-F-benzyl-, 2-F-6-MeO-benzyl-, 2,6-diMeO-benzyl-, 2,5-diMeO-benzyl-, 2-MeO-6-F-benzyl-, 2,5-diMeO-6-F-benzyl-, 2,3-diF-6-MeO-benzyl-, benzoyl-, —CH₂-pyrid-2-yl, —CH₂(2-Me-thiazol-5-yl), —CH₂(5-Me-pyrid-2-yl), —CH₂(6-Cl-pyrid-2-yl), —CH₂-thien-2-yl, —CH₂-thien-3-yl, —CH₂(4-Br-thien-2-yl), —CH₂-furan-2-yl, —CH₂CH=CH-furan-2-yl, —CH₂(3-MeO-pyrid-2-yl), and —CH₂-(5-Cl-2,3-thiadiazol-4-yl); and R[11] is H, cyclopropyl, CH₃, C₂H₅, CH(CH₃)₂, n-propyl, n-butyl, or iso-butyl.

[6] In a further preferred embodiment, wherein the compound is of Formula (IC)

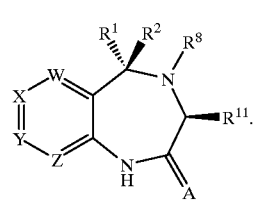

[7] In a further preferred embodiment, wherein the compound is of Formula (Id):

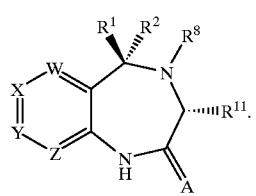

[8] In a further embodiment, wherein the compound is of Formula I(e):

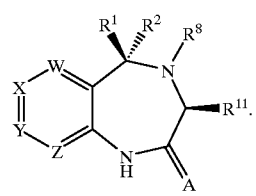

[9] In a further embodiment, wherein the compound is of Formula (If):

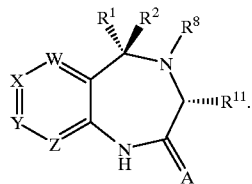

[10] In a further preferred embodiment, the compound of Formula (I) is selected from the group:

7-Chloro-4-butyl-1,5-dihydro-5-(trifluoromethyl)-1,4-benzodiazepin-2-one;

7-Chloro-4-(3-methyl-2-butenyl)-1,5-dihydro-5-(trifluoromethyl)-1,4-benzodiazepin-2-one;

7-Chloro-4-(2-pyridylmethyl)-1,5-dihydro-5-(trifluoromethyl)-1,4-benzodiazepin-2-one;

7-Chloro-4-(2-methyl-5-thiazolylmethyl)-1,5-dihydro-5-(trifluoromethyl)-1,4-benzodiazepin-2-one;

7-Chloro-4-(5-methyl-2-pyridylmethyl)-1,5-dihydro-5-(trifluoromethyl)-1,4-benzodiazepin-2-one;

7-Chloro-4-(6-chloro-2-pyridylmethyl)-1,5-dihydro-5-(trifluoromethyl)-1,4-benzodiazepin-2-one;

7-Chloro-4-propyl-1,5-dihydro-5-(trifluoromethyl)-1,4-benzodiazepin-2-one;

7-Chloro-4-hexyl-1,5-dihydro-5-(trifluoromethyl)-1,4-benzodiazepin-2-one;

7-Chloro-4-pentyl-1,5-dihydro-5-(trifluoromethyl)-1,4-benzodiazepin-2-one;

7-Chloro-4-(3-phenylpropyl)-1,5-dihydro-5-(trifluoromethyl)-1,4-benzodiazepin-2-one;

7-Chloro-4-benzyl-1,5-dihydro-5-(trifluoromethyl)-1,4-benzodiazepin-2-one;

7-Chloro-4-pentyl-1,5-dihydro-5-(trifluoromethyl)-1,4-benzodiazepin-2-one;

7-Chloro-4-(5-pentenyl)-1,5-dihydro-5-(trifluoromethyl)-1,4-benzodiazepin-2-one;

7-Chloro-4-(2-methylbenzyl)-1,5-dihydro-5-(trifluoromethyl)-1,4-benzodiazepin-2-one;

7-Chloro-4-(2-bromobenzyl)-1,5-dihydro-5-(trifluoromethyl)-1,4-benzodiazepin-2-one;

7-Chloro-4-(2-chloro-6-fluorobenzyl)-1,5-dihydro-5-(trifluoromethyl)-1,4-benzodiazepin-2-one;

7-Chloro-4-(2-cyanobenzyl)-1,5-dihydro-5-(trifluoromethyl)-1,4-benzodiazepin-2-one;

7-Chloro-4-(2,6-difluorobenzyl)-1,5-dihydro-5-(trifluoromethyl)-1,4-benzodiazepin-2-one;

7-Chloro-4-(3-methoxybenzyl)-1,5-dihydro-5-(trifluoromethyl)-1,4-benzodiazepin-2-one;

7-Chloro-4-(2,6-diclorobenzyl)-1,5-dihydro-5-(trifluoromethyl)-1,4-benzodiazepin-2-one;

7-Chloro-4-(3-cyanobenzyl)-1,5-dihydro-5-(trifluoromethyl)-1,4-benzodiazepin-2-one;

7-Chloro-4-(2-methoxybenzyl)-1,5-dihydro-5-(trifluoromethyl)-1,4-benzodiazepin-2-one;

7-Chloro-4-(2-thienylmethyl)-1,5-dihydro-5-(trifluoromethyl)-1,4-benzodiazepin-2-one;

7-Chloro-4-(3-thienylmethyl)-1,5-dihydro-5-(trifluoromethyl)-1,4-benzodiazepin-2-one;

7-Chloro-4-(2-furanylmethyl)-1,5-dihydro-5-(trifluoromethyl)-1,4-benzodiazepin-2-one;

7-Chloro-4-(3-methylpentyl)-1,5-dihydro-5-(trifluoromethyl)-1,4-benzodiazepin-2-one;

7-Chloro-4-(3-methoxy-2-pyridylmethyl)-1,5-dihydro-5-(trifluoromethyl)-1,4-benzodiazepin-2-one;

7-Chloro-4-(3-cyclopropyl-2-propynyl)-1,5-dihydro-5-(trifluoromethyl)-1,4-benzodiazepin-2-one;

7-Chloro-5-butyl-1,5-dihydro-5-(trifluoromethyl)-1,4-benzodiazepin-2-one;

7-Chloro-4-(2-hexynyl)-1,5-dihydro-5-(trifluoromethyl)-1,4-benzodiazepin-2-one;

7-Chloro-4-(4-methyl-2-pentynyl)-1,5-dihydro-5-(trifluoromethyl)-1,4-benzodiazepin-2-one;

7-Chloro-4-(3-methylpentyl)-1,5-dihydro-5-(trifluoromethyl)-1,4-benzodiazepin-2-one;

6,7-Difluoro-4-(2-fluoro-6-methoxybenzyl)-1,5-dihydro-5-(trifluoromethyl)-1,4-benzodiazepin-2-one;

6,7-Difluoro-4-hydroxy-5-(3-methyl-1-butynyl)-1,5-dihydro-5-(trifluoromethyl)-1,4-benzodiazepin-2-one;

7-Chloro-5-(3-methyl-1-butynyl)-1,5-dihydro-5-(trifluoromethyl)-1,4-benzodiazepin-2-one;

7-Chloro-5-(2-thienylethynyl)-1,5-dihydro-5-(trifluoromethyl)-1,4-benzodiazepin-2-one;

7-Chloro-4-butyl-5-(3-methyl-1-butynyl)-1,5-dihydro-5-(trifluoromethyl)-1,4-benzodiazepin-2-one;

7-Chloro-4-(2-fluorobenzyl)-1,5-dihydro-5-(trifluoromethyl)-1,4-benzodiazepin-2-one;

7-Chloro-4-(2-(2-chlorophenyl)ethyl)-1,5-dihydro-5-(trifluoromethyl)-1,4-benzodiazepin-2-one;

7-Chloro-4-benzoyl-1,5-dihydro-5-(trifluoromethyl)-1,4-benzodiazepin-2-one;

7-Chloro-4-(2-(2-iodophenyl)ethyl)-1,5-dihydro-5-(trifluoromethyl)-1,4-benzodiazepin-2-one;

7-Chloro-4-(2-(3-chlorophenyl)ethyl)-1,5-dihydro-5-(trifluoromethyl)-1,4-benzodiazepin-2-one;

7-Chloro-4-(3-fluorobenzyl)-1,5-dihydro-5-(trifluoromethyl)-1,4-benzodiazepin-2-one;

7-Chloro-4-(2,6-dimethoxybenzyl)-1,5-dihydro-5-(trifluoromethyl)-1,4-benzodiazepin-2-one;

7-Chloro-4-(2,5-dimethoxybenzyl)-1,5-dihydro-5-(trifluoromethyl)-1,4-benzodiazepin-2-one;

7-Chloro-4-(2,5-dimethoxy-6-fluorobenzyl)-1,5-dihydro-5-(trifluoromethyl)-1,4-benzodiazepin-2-one;

7-Chloro-4-(2-methoxy-6-fluorobenzyl)-1,5-dihydro-5-(trifluoromethyl)-1,4-benzodiazepin-2-one;

7-Chloro-4-(2,3-difluorobenzyl)-1,5-dihydro-5-(trifluoromethyl)-1,4-benzodiazepin-2-one;

7-Chloro-4-(2,5-difluorobenzyl)-1,5-dihydro-5-(trifluoromethyl)-1,4-benzodiazepin-2-one;

7-Chloro-4-(2-pentynyl)-1,5-dihydro-5-(trifluoromethyl)-1,4-benzodiazepin-2-one;

7-Chloro-4-(4-bromothien-2-ylmethyl)-1,5-dihydro-5-(trifluoromethyl)-1,4-benzodiazepin-2-one;

7-Chloro-4-(3-methylbutyl)-1,5-dihydro-5-(trifluoromethyl)-1,4-benzodiazepin-2-one;

7-Chloro-4-(4-penten-1-yl)-1,5-dihydro-5-(trifluoromethyl)-1,4-benzodiazepin-2-one;

7-Chloro-4-(2-penten-1-yl)-1,5-dihydro-5-(trifluoromethyl)-1,4-benzodiazepin-2-one;

7-Chloro-4-(3-phenyl-2-propynyl)-1,5-dihydro-5-(trifluoromethyl)-1,4-benzodiazepin-2-one;

7-Chloro-4-(4-(5-chloro-2,3-thiadiazole)methyl)-1,5-dihydro-5-(trifluoromethyl)-1,4-benzodiazepin-2-one;

7-Chloro-4-(3-(2-furanyl)-2-propenyl)-1,5,-dihydro-5-(trifluoromethyl)-1,4-benzodiazepin-2-one;

7-Chloro-4-(2,3-difluoro-6-methoxybenzyl)-1,5-dihydro-5-(trifluoromethyl)-1,4-benzodiazepin-2-one;

7-Chloro-4-(2-fluoro-6-methoxybenzyl)-1,5-dihydro-5-(trifluoromethyl)-1,4-benzodiazepin-2-one;

7-Chloro-5-phenyl-5-butyl-1,5-dihydro-5-(trifluoromethyl)-1,4-benzodiazepin-2-one;

7-Chloro-4-(2-pentynyl)-1,5-dihydro-5-(trifluoromethyl)-1,4-benzodiazepin-2-one;

7-Chloro-5-(cyclopropylethynyl)-1,5-dihydro-5-(trifluoromethyl)-1,4-benzodiazepin-2-one;

7-Chloro-4-phenyl-1,5-dihydro-5-(trifluoromethyl)-1,4-benzodiazepin-2-one;

7-Chloro-4-(2-propynyl)-1,5-dihydro-5-(trifluoromethyl)-1,4-benzodiazepin-2-one;

7-Chloro-4-(2-butynyl)-1,5-dihydro-5-(trifluoromethyl)-1,4-benzodiazepin-2-one;

7-Chloro-5-(2-cyclopropyl-2-ethanonyl)-1,5-dihydro-5-(trifluoromethyl)-1,4-benzodiazepin-2-one;

7-Chloro-5-benzyl-1,5-dihydro-5-(trifluoromethyl)-1,4-benzodiazepin-2-one;

7-Chloro-5-(2-methylpropyl)-1,5-dihydro-5-(trifluoromethyl)-1,4-benzodiazepin-2-one;

7-Chloro-5-(2-phenylethyl)-1,5-dihydro-5-(trifluoromethyl)-1,4-benzodiazepin-2-one;

7-Chloro-3-methyl-5-(4-methylbutyl)-1,5-dihydro-5-(trifluoromethyl)-1,4-benzodiazepin-2-one;

7-Chloro-3-methyl-5-(cyclopropylethynyl)-1,5-dihydro-5-(trifluoromethyl)-1,4-benzodiazepin-2-one;

7-Chloro-5-(cyclopropylethynyl)-1,5-dihydro-5-(trifluoromethyl)-1,4-benzodiazepin-2-one;

7-Chloro-5(S)-(cyclopropylethynyl)-1,5-dihydro-5-(trifluoromethyl)-1,4-benzodiazepin-2-one;

7-Chloro-4-methyl-5-(cyclopropylethynyl)-1,5-dihydro-5-(trifluoromethyl)-1,4-benzodiazepin-2-one;

7-Chloro-3-(2-methylpropyl)-5-pentyl-1,5-dihydro-5-(trifluoromethyl)-1,4-benzodiazepin-2-one;

7-Chloro-3-methyl-5-(2-cyclopropylethynyl)-1,5-dihydro-5-(trifluoromethyl)-1,4-benzodiazepin-2-one;

7-Chloro-5-pentyl-1,5-dihydro-5-(trifluoromethyl)-1,4-benzodiazepin-2-one;

7-Chloro-4-(2-fluoro-6-methylbenzyl)-1,5-dihydro-5-(trifluoromethyl)-1,4-benzodiazepin-2-one;

3-Methyl-5-pentyl-1,5-dihydro-5-(trifluoromethyl)-1,4-benzodiazepin-2-one;

7-Chloro-3-methyl-5-(2-cyclopropylethynyl)-1,5-dihydro-5-(trifluoromethyl)-1,4-benzodiazepin-2-one;

3(R)-Methyl-5-(2-cyclopropylethynyl)-1,5-dihydro-5-(trifluoromethyl)-1,4-benzodiazepin-2-one;

3(S)-Methyl-5-(cyclopropylethynyl)-1,5-dihydro-5-(trifluoromethyl)-1,4-benzodiazepin-2-one;

3-Ethyl-5-(cyclopropylethynyl)-1,5-dihydro-5-(trifluoromethyl)-1,4-benzodiazepin-2-one;

7-Chloro-5-pentyl-1,5-dihydro-5-(trifluoromethyl)-1,4-benzodiazepin-2-one;

7-Chloro-5-(3-methylbutyl)-1,5-dihydro-5-(trifluoromethyl)-1,4-benzodiazepin-2-one;

7-Chloro-5-benzyl-1,5-dihydro-5-(trifluoromethyl)-1,4-benzodiazepin-2-one;

7-Chloro-5-(2-cyclopropyl-E-ethenyl)-1,5-dihydro-5-(trifluoromethyl)-1,4-benzodiazepin-2-one;

7-Chloro-5-hexyl-1,5-dihydro-5-(trifluoromethyl)-1,4-benzodiazepin-2-one;

7-Chloro-5-(2-cyclopropylethyl)-1,5-dihydro-5-(trifluoromethyl)-1,4-benzodiazepin-2-one;

7-Chloro-3-methyl-5-(2-cyclopropylethyl)-1,5-dihydro-5-(trifluoromethyl)-1,4-benzodiazepin-2-one;

6,7-Difluoro-5-(2-cyclopropylethynyl)-1,5-dihydro-5-(trifluoromethyl)-1,4-benzodiazepin-2-one;

7-Chloro-5-(cyclopropylmethyl)-1,5-dihydro-5-(trifluoromethyl)-1,4-benzodiazepin-2-one;

7-Chloro-5-(4,4,4-trifluorobutyl)-1,5-dihydro-5-(trifluoromethyl)-1,4-benzodiazepin-2-one;

7-Methoxy-5-(cyclopropylethynyl)-1,5-dihydro-5-(trifluoromethyl)-1,4-benzodiazepin-2-one;

7-Fluoro-5-(cyclopropylethynyl)-1,5-dihydro-5-(trifluoromethyl)-1,4-benzodiazepin-2-one;

7-Fluoro-5-(2-cyclopropyl-Z-ethenyl)-1,5-dihydro-5-(trifluoromethyl)-1,4-benzodiazepin-2-one;

6,7-Difluoro-5-(3,3,3-trifluoropropyl)-1,5-dihydro-5-(trifluoromethyl)-1,4-benzodiazepin-2-one;

7-Chloro-5-(2-pyridylmethyl)-1,5-dihydro-5-(trifluoromethyl)-1,4-benzodiazepin-2-one;

7-Chloro-5-butyl-1,5-dihydro-5-(trifluoromethyl)-1,4-benzodiazepin-2-one;

or a pharmaceutically acceptable salt form thereof.

In a third embodiment, the present invention provides a novel pharmaceutical composition comprising a pharmaceutically acceptable carrier and a therapeutically effective amount of a compound of Formula (I) or pharmaceutically acceptable salt form thereof.

In a fourth embodiment, the present invention provides a novel method for treating HIV infection which comprises administering to a host in need of such treatment a therapeutically effective amount of a compound of Formula (I) or pharmaceutically acceptable salt form thereof.

In a fifth embodiment, the present invention provides a novel method of treating HIV infection which comprises administering, in combination, to a host in need thereof a therapeutically effective amount of:

(a) a compound of Formula (I); and, (b) at least one compound selected from the group consisting of HIV reverse transcriptase inhibitors and HIV protease inhibitors.

In another preferred embodiment, the reverse transcriptase inhibitor is selected from the group AZT, ddC, ddI, d4T, 3TC, delavirdine, efavirenz, nevirapine, Ro 18,893, trovirdine, MKC-442, HBY 097, ACT, UC-781, UC-782, RD4-2025, and MEN 10979, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In an even more preferred embodiment, the reverse transcriptase inhibitor is selected from the group AZT, efavirenz, and 3TC and the protease inhibitor is selected from the group saquinavir, ritonavir, nelfinavir, and indinavir.

In a still further preferred ebodiment, the reverse transcriptase inhibitor is AZT.

In another still further preferred embodiment, the protease inhibitor is indinavir.

In a sixth embodiment, the present invention provides a pharmaceutical kit useful for the treatment of HIV infection, which comprises a therapeutically effective amount of:

(a) a compound of Formula (I); and, (b) at least one compound selected from the group consisting of HIV reverse transcriptase inhibitors and HIV protease inhibitors, in one or more sterile containers.

In a seventh embodiment, the present invention provides novel 1,4-benzodiazepin-2-ones for use in therapy.

In a eighth embodiment, the present invention provides the use of novel 1,4,-benzodiazepin-2-ones for the manufacture of a medicament for the treatment of HIV infection.

DEFINITIONS

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

As used herein, $R^1$ is a substituent in the 5 position of the bicyclic compound of Formula (I) and is selected from the group cyclopropyl and $C_{1-3}$ alkyl substituted with 0–7 halogen. A preferred definition of $R^1$ is selected from the group cyclopropyl and $C_{1-3}$ alkyl substituted with 1–7 halogen; further preferred is $C_{1-3}$ alkyl substituted with 2–7 halogen; more preferred is $C_{1-3}$ alkyl substituted with 3–7 halogen. Examples of preferred $R^1$ are $CHF_2$, $CF_3$, $CF_2CF_3$, and $CF_2CF_2CF_3$; further preferred are $CHF_2$, $CF_3$, and $CF_2CF_3$; more preferred is $CF_3$ and $CF_2CF_3$; and even more preferred is $CF_3$.

As used herein, preferred examples of $R^3$ and $R^{3a}$ are H, methyl, ethyl, OH, methoxy, ethoxy, F, and Cl; more preferred are H, methyl, OH, methoxy, F, and Cl. Preferred examples of $R^{3b}$ and $R^{3c}$ are H, methyl, OH, methoxy, F, and Cl; more preferred is H.

As used herein, $R^2$ is a substituent attached to the 5 position of the bicyclic compound of Formula (I) and is selected from H or a chemical moiety attached through a carbon, oxygen, sulphur, or nitrogen. A preferred definition of $R^2$ is H or a chemical moiety attached through a carbon or oxygen; more preferred is H or a chemical moiety attached through a carbon atom; even more preferred is H, a substituted alkyl, a substituted alkenyl, or a substituted alkynyl. Preferred examples of $R^2$ are H, methyl-, ethyl-, propyl-, butyl-, pentyl-, hexyl-, $CF_3CH_2CH_2$—, CF$_3$CH$_2$CH$_2$CH$_2$—, PhCH$_2$—, PhCH$_2$CH$_2$—, cycPr—CH$_2$—, cycPr—CH$_2$CH$_2$—, pyrid-2-yl-CH$_2$—, cycPr—C(=O)CH$_2$—, -, cycPr—CH=CH—, -, iPr—C≡C—, cycpr—C≡C—, and thien-2-yl-C≡C—.

As used herein, "alkyl" is intended to include both branched and straight-chain saturated aliphatic hydrocarbon groups having the specified number of carbon atoms. C$_{1-10}$ alkyl, is intended to include C$_1$, C$_2$, C$_3$, C$_4$, C$_5$, C$_6$, C$_7$, C$_8$, C$_9$, and C$_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. C$_{1-10}$ alkoxy, is intended to include C$_1$, C$_2$, C$_3$, C$_4$, C$_5$, C$_6$, C$_7$, C$_8$, C$_9$, and C$_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. C$_{3-7}$ cycloalkyl, is intended to include C$_3$, C$_4$, C$_5$, C$_6$, and C$_7$ cycloalkyl groups. Alkenyl" is intended to include hydrocarbon chains of either a straight or branched configuration and one or more unsaturated carbon-carbon bonds which may occur in any stable point along the chain, such as ethenyl, propenyl and the like. C$_{2-10}$ alkenyl, is intended to include C$_2$, C$_3$, C$_4$, C$_5$, C$_6$, C$_7$, C$_8$, C$_9$, and C$_{10}$ alkenyl groups. "Alkynyl" is intended to include hydrocarbon chains of either a straight or branched configuration and one or more triple carbon-carbon bonds which may occur in any stable point along the chain, such as ethynyl, propynyl and the like. C$_{2-10}$ alkynyl, is intended to include C$_2$, C$_3$, C$_4$, C$_5$, C$_6$, C$_7$, C$_8$, C$_9$, and C$_{10}$ alkynyl groups.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3, 4, 5, 6, or 7-membered monocyclic or bicyclic or 7, 8, 9, 10, 11, 12 or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, or tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), efavirenz (DuPont), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. In the Schemes which follow, $R^1$ is shown as a $CF_3$ group, but could be any one of the presently described $R^1$ groups.

Scheme 1

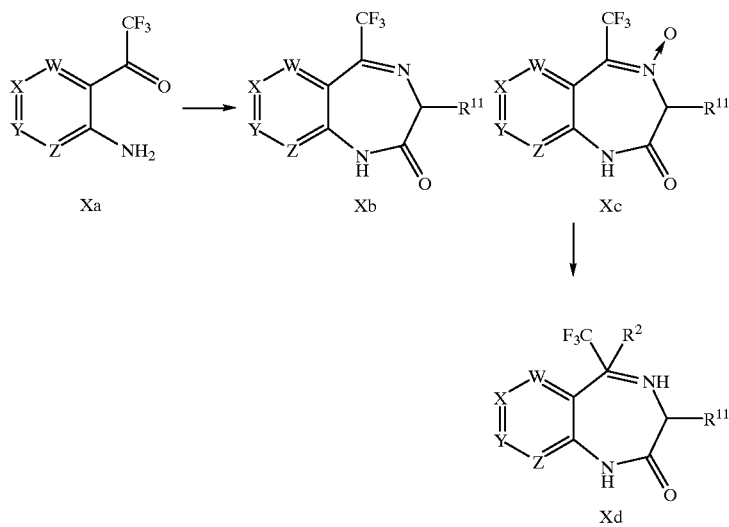

Scheme 1 illustrates a method of making a variety of 1,4-benzodiazepin-2-ones. An appropriately substituted amino-ketone is acylated and cyclized in the presence of titanium tetrachloride to give Xb which is first reduced to the amine and then oxidized to give oxide Xc. The oxide Xc is reacted with a lithium or grignard reagent to give Xd.

Scheme 2

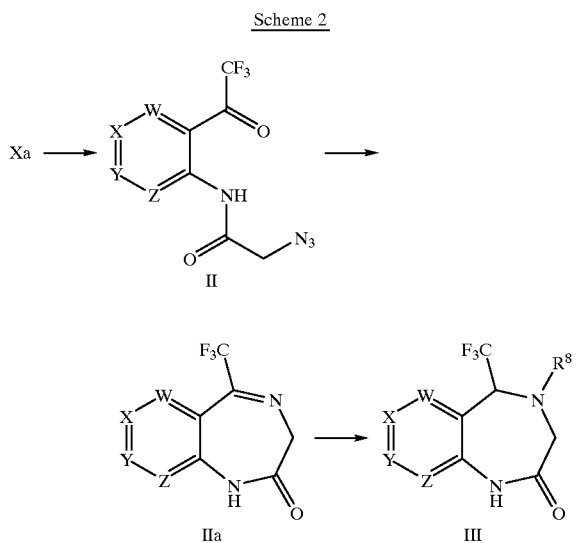

Scheme 2 depicts a method of forming 1,4-benzodiazepin-2-one III. Compound Xa is first acylated with the acid chloride or bromide which is then reacted with sodium azide. Cyclization gives intermediate IIa which can be reduced with sodium cyanoborohydride and alkylated using an appropriate aldehyde to give III.

Scheme 3

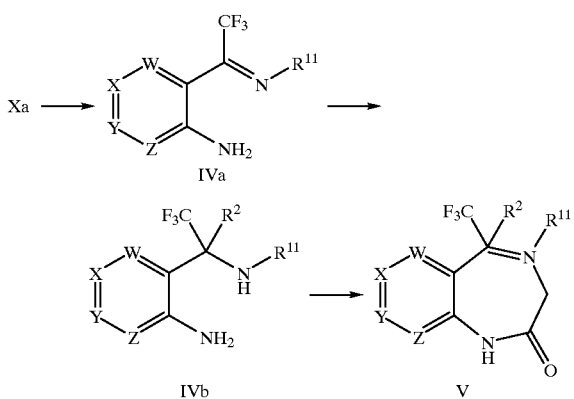

Scheme 3 illustrates a method of first reacting Xa with the appropriate amine and titanium tetrachloride to give the imine IVa. The imine is either reduced to the amine or alkylated with an organomettalic reagent to give IVb. Cyclization is then accomplished using the bromoacetyl bromide to give V.

Scheme 4

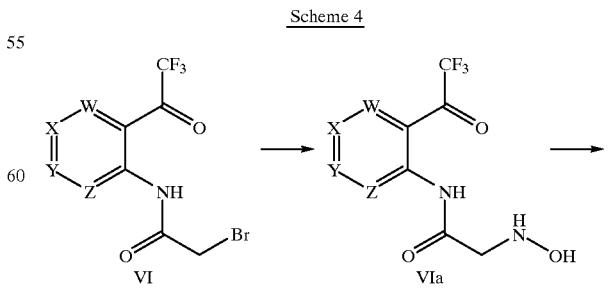

-continued

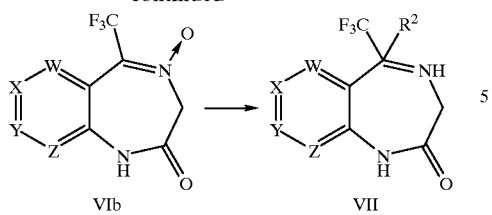

VIb                    VII

Scheme 4 illustrates a method of preparing 1,4-diazapenin-2-ones by first reacting the acylated aniline VI with hydroxylamine to give intermediate VIa which is cyclized by acetic acid to give VIb. The intermediate VIb is then reacted with an appropriate organometallic reagent to give VII.

Scheme 5

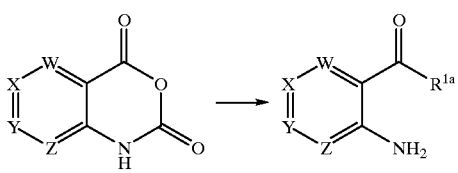

In addition to the methods of obtaining keto-anilines described previously, nucleophilic opening of isatoic anhydrides can also be used as shown in Scheme 5. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

One enantiomer of a compound of Formula (I) may display superior activity compared with the other. Thus, the following stereochemistries are considered to be a part of the present invention.

Ic

Id

Ie

If

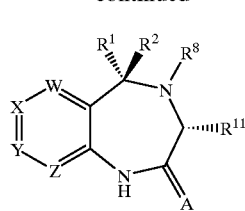

When required, separation of the diasteriomeric material can be achieved by HPLC using a chiral column or by a resolution using a resolving agent such as camphonic chloride as in Thomas J. Tucker, et al, *J. Med. Chem.* 1994, 37, 2437–2444. A chiral compound of Formula (I) may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "ACN" for acetic anhydride, "CDI" for carbonyl diimidazole, "DIEA" for diisopropylethylamine, "DIPEA" for diisopropylethylamine, "DMAP" for dimethylaminopyridine, "DME" for dimethoxyethane, "EDAC" for 1-(3-dimethylaminopropyl)-3-ethylcarbodiimide hydrochloride, "LAH" for lithium aluminium hydride, "TBAF" for tetrabutylammonium fluoride, "TBS-Cl" for t-butyldimethylsilyl chloride, and "TEA" for triethylamine.

All reactions were run under a nitrogen atmosphere at room temperature and most were not optimized. The reactions were followed by TLC. Reactions run over night were done so for adequate time. Reagents were used as received. Dimethylformamide, tetrahydrofuran and acetonitrile were dried over molecular sieves. All other solvents were reagent grade. Ethanol and methanol were absolute and water was deionized. Melting points were determined in open capillary tubes on a Mel-Temp apparatus and are uncorrected. Column chromatographies were done on flash silica gel. Exceptions to any of the conditions above are noted in the text. Ciral HPLC separations were done using ciral columns which gave the enantiomers in >99% EE.

Example 1

Synthesis of 4-substituted 1,4-benzodiazepin-2-ones.

Method AA; The chloroacetyl chloride (540 μL, 6.8 mmol) was added to a biphasic mixture of 1 (1.2 g, 5.2 mmol) in dichloromethane (10 mL) and 10% potassium carbonate (15 mL) and the reaction was stirred for 30 minutes. The reaction was diluted with ether (30 mL), washed with saturated sodium bicarbonate (3×25 mL) and saturated NaCl (5 mL), dried (MgSO$_4$) and evaporated at reduced pressure giving 2A as a light yellow oil that was used without further purification.

Method A; The bromoacetyl bromide (5.9 mL, 68 mmol) was added to a solution of 1 (13 g, 57 mmol) and pyridine (6.4 mL, 79 mmol) in dichloromethane (130 mL) and the reaction was stirred for 30 minutes. The reaction was diluted with ethyl acetate (100 mL), washed with 1N HCl (2×80 mL), saturated sodium bicarbonate (80 mL) and saturated NaCl (20 mL), dried (MgSO$_4$) and evaporated at reduced pressure giving 2 as a light yellow oil that was used without further purification Method B; A solution of 2 (1.54 g, 5.13 mmol) and sodium azide (367 mg, 5.65 mmol) in N,N-dimethylformamide (15 mL) was stirred for one hour. The reaction was diluted with ethyl acetate (50 mL), washed with water (3×40 mL) and saturated NaCl (10 mL), dried (MgSO$_4$) and evaporated at reduced pressure giving 3 as a yellow oil that was used without further purification.

Method C; A solution of 3 (5.13 mmol) and triphenylphosphene (1.48 g, 5.65 mmol) in tetrahydrofuran (15 mL) was stirred over night. The reaction was evaporated at reduced pressure and chromatography of the residue (hexane/ethyl acetate, 50%) gave a creamy foam that was crystallized from dichloromethane/cyclohexane giving 4 as slightly yellow needles, 1.01 g (53% for steps A–C).

Method D; The sodium cyanoborohydride (excess) was added to a solution of 4 (890 mg, 3.40 mmol) and acetic acid (612 mg, 10.3 mmol) in methanol (15 mL) and the reaction was stirred for one hour. The reaction was diluted with ethyl acetate (50 mL), washed with saturated sodium bicarbonate (3×40 mL) and saturated NaCl (10 mL), dried (MgSO$_4$) and evaporated at reduced pressure giving a light yellow crystalline mass. It was recrystallized from dichloromethane giving 5 as white plates, 690 mg (77%).

Method DD; A mixture of 16 (1.02 g), excess ammonium formate and 10% palladium on carbon (112 mg) in methanol (15 mL) and the reaction was stirred for three hours. It was filtered though celite, diluted with ethyl acetate (50 mL), washed with saturated sodium bicarbonate (3×40 mL) and saturated NaCl (10 mL), dried (MgSO$_4$) and evaporated at reduced pressure giving 17A as a light yellow powder that was used without further purification.

Method E; The sodium triacetoxyborohydride (16.0 g, 76 mmol) was added to a solution of 5 (4.04 g, 15.3 mmol), R-aldehyde (2-fluoro-6-methoxybenzaldehyde, 4.93 g, 32.0 mmol) and acetic acid (1.74 mL, 30.4 mmol) in dichloromethane (50 mL) and the reaction was stirred over night. The reaction was diluted with ethyl acetate (60 mL), washed with 1N HCl (2×50 mL), saturated sodium bicarbonate (50 mL) and saturated NaCl (10 mL), dried (MgSO$_4$) and evaporated at reduced pressure which gave thick yellow oil. It was crystallized from ether/petroleum ether giving 6 as a crystalline powder, 5.72 g (93%).

Method EE; The sodium cyanoborohydride (excess) was added to a solution of 5 (132 mg, 0.50 mmol), R-aldehyde (isopentyl aldehyde, 321 μg, 3.0 mmol) and acetic acid (29 μL, 0.50 mmol) in methanol (3 mL) and the reaction was stirred over night. The reaction was diluted with ethyl acetate (30 mL), washed with saturated sodium bicarbonate (3×25 mL) and saturated NaCl (10 mL), dried (MgSO$_4$) and evaporated at reduced pressure which gave thick yellow film. Chromatography (hexane/ethyl acetate, 30%) gave a colorless film. It was crystallized from methanol/water giving 6 as a crystalline powder, 90 mg (54%).

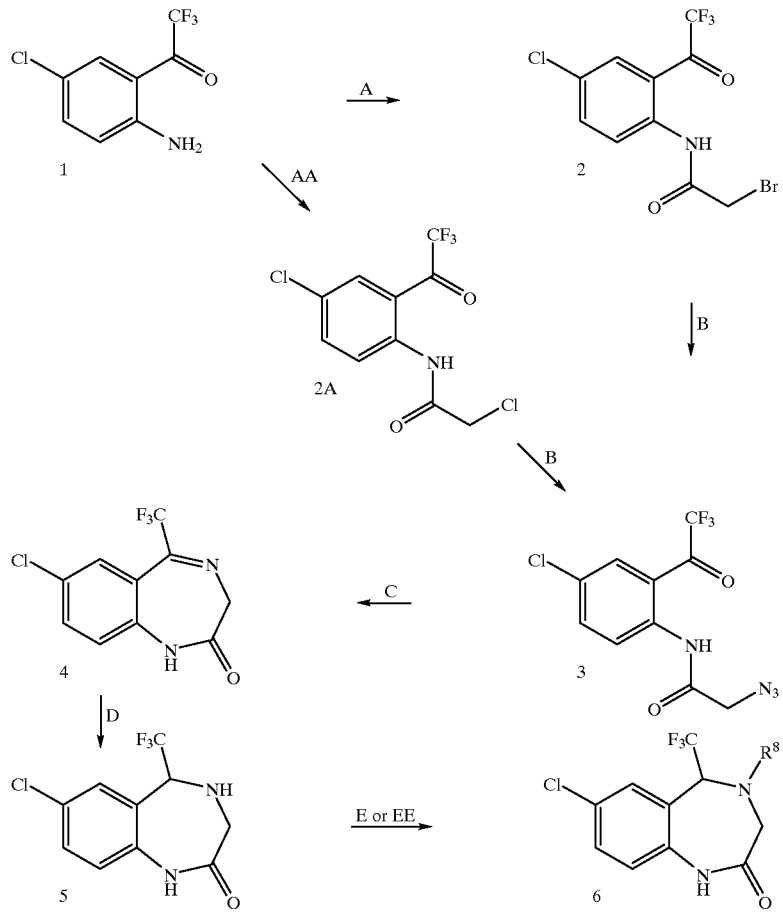

Example 2

The synthesis of 4-substituted 1,4-benzodiazepin-2-one.

Method F; A solution of 4 (619 mg, 2.24 mmol), SEM-chloride (474 μL, 2.69 mmol) and diisopropylethylamine (546 μL, 3.14 mmol) in dichloromethane (10 mL) was stirred over night. The reaction was diluted with ether (30 mL), washed with 1N HCl (3×25 mL) and saturated NaCl (5 mL), dried (MgSO$_4$) and evaporated at reduced pressure which gave 7 as a thick yellow oil that was used without further purification.

Intermediate 7 is converted to 8 using Method D.

Method G; A mixture of 8 (200 mg, 0.51 mmol), R-chloride (2-fluoro-3,6-dimethoxybenzyl chloride, 124 mg, 0.61 mmol), diisopropylethylamine (115 μL, 0.66 mmol) and potassium iodide (100 mg, 0.60 mmol) in N-methyl-2-pyrrolidinone or DMF (3 mL) was stirred at 110° C. over night. The reaction was diluted with ether (30 mL), washed with 1N HCl (3×25 mL) and saturated NaCl (5 mL), dried (MgSO$_4$) and evaporated at reduced pressure giving 9 as a yellow foam that was used without further purification.

Method GG; To a solution of pent-2-ynol (211 μL, 2.28 mmol), diisopropylethylamine (530 μL, 3.04 mmol) and methanesulfonyl chloride (156 μg, 2.03 mmol) in N-methyl-2-pyrrolidinone (3 mL) that had stirred for 40 minutes, was added 8 (200 mg, 0.51 mmol) as a solution in N-methyl-2-pyrrolidinone (1 mL) and the reaction was stirred at 85° C. over night. The reaction was diluted with ethyl acetate (30 mL), washed with 1N HCl (3×25 mL) and saturated NaCl (5 mL), dried (MgSO$_4$) and evaporated at reduced pressure giving 9 as a yellow oil that was used without further purification.

Method H; A solution of 9 (0.51 mmol) in trifluoroacitic acid (2 mL) was stirred for 30 minutes. The reaction was diluted with ethyl acetate (30 mL), washed with saturated sodium bicarbonate (3×25 mL) and saturated NaCl (5 mL), dried (MgSO$_4$) and evaporated at reduced pressure which gave an orange film. The N-hydroxymethyl intermediate was stirred in methanol (5 mL) with saturated sodium bicarbonate or 10% NaOH (0.5 mL) for 15 minutes. The reaction was diluted with ethyl acetate (30 mL), washed with saturated sodium bicarbonate (3×25 mL) and saturated NaCl (5 mL), dried (MgSO$_4$) and evaporated at reduced pressure which gave a yellow foam. Chromatography of the foam (ether/hexane, 30%) gave a creamy white powder. It was crystallized from ether/petroleum ether giving 10 as a white crystalline powder, 78 mg (36% for steps F,G and H).

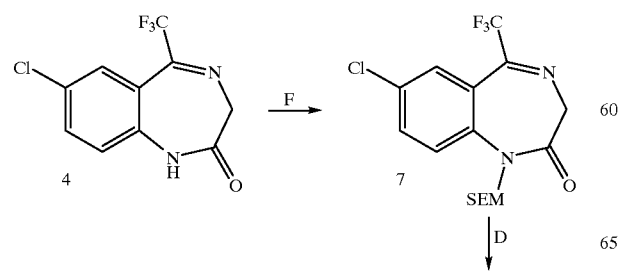

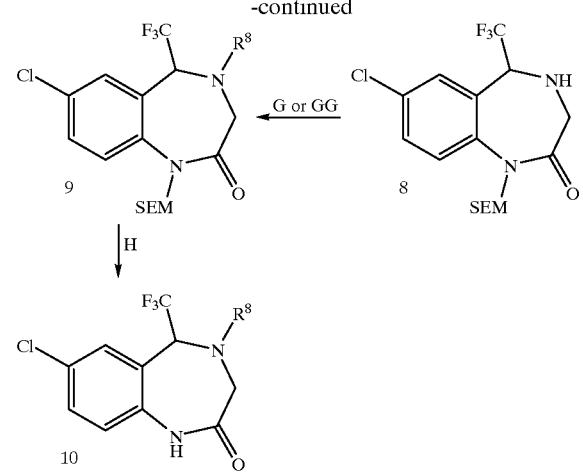

Example 3

Synthesis of 4-substituted 1,4-benzodiazepin-2-ones.

Method I; The acid R-chloride (benzoyl chloride, 115 μL, 0.67 mmol) was added to a solution of 8 (200 mg, 0.51 mmol) and diisopropylethylamine (115 μL, 0.66 mmol) in dichloromethane (3 mL) and the reaction was stirred for 1 hour. The reaction was diluted with ether (30 mL), washed with 1N HCl (3×25 mL) and saturated NaCl (5 mL), dried (MgSO$_4$) and evaporated at reduced pressure giving 11 as a thick honey colored oil that was used without further purification.

Compound 11 was converted to Compound 12 using Method H.

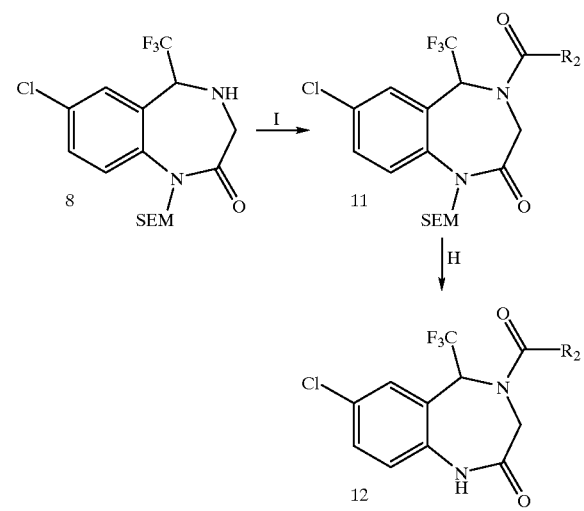

Example 4

Synthesis of 5-substituted 1,4-benzodiazapin-2-ones.

Method J; A solution of 2 (10.2 g, 28.4 mmol), hydroxyl amine hydrochloride (5.88 g, 85.2 mmol) and diisopropylethylamine (14.8 mL, 85.2 mmol) in N-methyl-2-pyrrolidinone EtOH (100 mL) was stirred for 6 hours. The reaction was diluted with ethyl acetate (100 mL), washed with water (3×75 mL) and saturated NaCl (20 mL), dried (MgSO$_4$) and evaporated at reduced pressure which gave a yellow crystalline mass. It was tricherated in dichloromethane giving 13 as a yellow crystalline powder, 7.91 g (94%).

Method K; A solution of 13 (1.45 g) in acetic acid and dichloromethane (10 mL of each) was stirred over night. The reaction was diluted with ethyl acetate (30 mL), washed with saturated sodium bicarbonate (3×25 mL) and saturated NaCl (5 mL), dried (MgSO$_4$) and evaporated at reduced pressure which gave a yellow solid. It was crystallized from ethyl acetate/hexane giving 14 as yellow needles, 0.991 g (73%).

Method L; A concentrated solution of 14 (2.10 g, 7.55 mmol) in tetrahydrofuran (5 mL) was added to a chilled (−78° C.) solution of the organometalic reagent (lithium acetylide, 37.8 mmol) in tetrahydrofuran (20 mL) and the reaction was stirred for 30 minutes warming to 0° C. Then carbon disulfide (2.79 mL, 45.3 mmol) was added to the reaction and it was stirred for an additional hour. The reaction was quenched with saturated ammonium chloride then diluted with ethyl acetate (50 mL), washed with 1N sodium hydroxide (3×30 mL) and saturated NaCl (10 mL), dried (MgSO$_4$), clarified with activated charcoal/celite and evaporated at reduced pressure giving a red oil with crystals. Recrystallization from dichloromethane/hexane gave 15 as a creamy white powder, 1.72 g (69%).

dine (19.5 mL, 112 mmol) and aminoester hydrochloride (d-alanine methylester hydrochloride, 3.43 g, 24.7 mmol) in dichloromethane (50 mL) and the reaction was stirred for three hours. The reaction was diluted with ethyl acetate (60 mL), washed with 1N HCl (2×50 mL), saturated sodium bicarbonate (50 mL) and saturated NaCl (10 mL), dried (MgSO$_4$) and evaporated at reduced pressure giving a honey colored foam. It was crystallized from dichloromethane/hexane giving 16 as a creamy white powder, 3.25 g (53%).

Compound 16 was converted to 17 or 17A using Method D or Method DD.

Method N; A solution of 17 (9.51 g, 34.2 mmol) and meta-chloroperbenzoic acid (35.3 g, 103 mmol) in dichloromethane (200 mL) was stirred for six hours. The reaction was filtered though celite (removed meta-chlorobenzoic acid) and stirred with 10% sodium sulfite (50 mL) for ten minutes to convert excess perbenzoic acid to benzoic acid. It was washed with saturated sodium bicarbonate (3×80 mL) and saturated NaCl (30 mL), dried (MgSO$_4$) and evaporated at reduced pressure giving a red foam. It was crystallized from ethyl acetate/hexane giving 18 as a creamy powder, 7.03 g (71%).

Compound 18 was converted to compound 19 using Method L.

Method O; A solution of 19 (432 mg) and 1,8-diazebicyclo[5.4.0]undac-7-ene (5 drops) in dioxane (5 mL) was refluxed for eight hours. The reaction was diluted with

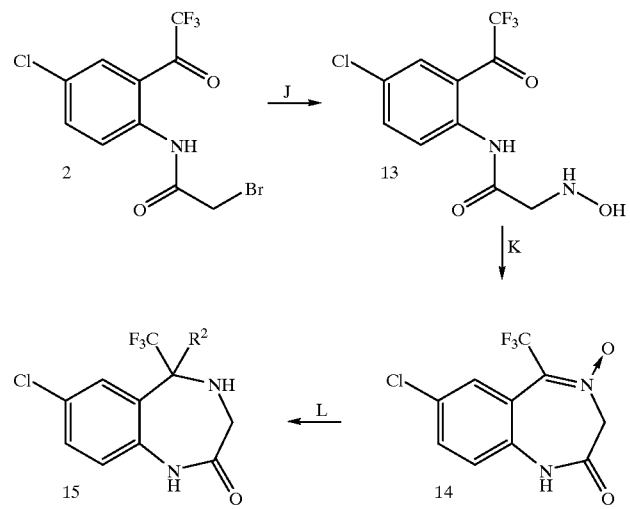

Example 5

Synthesis of 3,5-substitued 1,4-benzodiazapin-2-ones.

Method M; The titanium tetrachloride solution (4.9 mL, 44.8 mmol in dichloromethane, 50 mL) was added dropwise by way of a drop funnel to a solution of 1 (5.00 g, 22.4 mmol), diisopropylethylamine or 4-Me-2, 6-di-t-Bu pyriethyl acetate (30 mL), washed saturated sodium bicarbonate (3×25 mL) and saturated NaCl (5 mL), dried (MgSO$_4$) and evaporated at reduced pressure giving a yellow film as a mixture; 1/4 starting material to product. Chromatography (hexane/ethyl acetate, 20 to 30%) gave a white powder. It was crystallized from dichloromethane/hexane giving 20 as white prisms. 223 mg (52%).

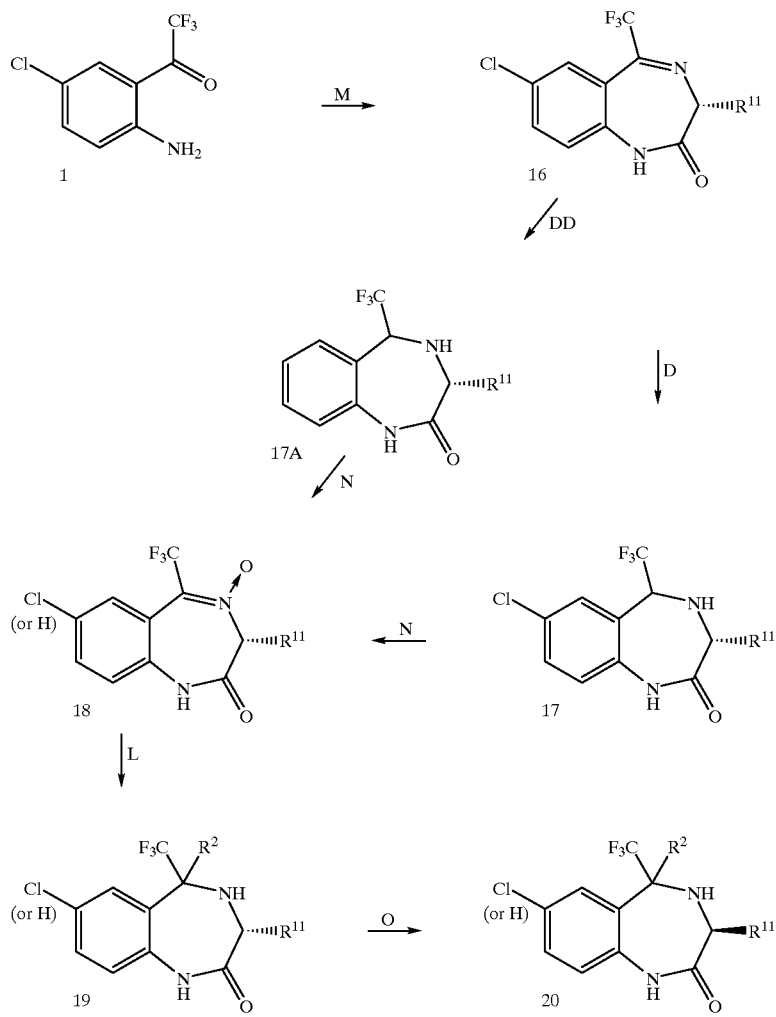

Example 6

Synthesis 3,5-substituted 1,4-benzodiazepin-2-ones.

Method P; A solution of 14 (152 mg, 0.520 mmol) in tetrahydrofuran (2 mL) was added to a chilled (0° C.) solution of the organometalic reagent (lithium or magnesium acetylide, 2.08 mmol) in tetrahydrofuran (5 mL) and the reaction was stirred for 30 minutes warming to room temperature. The reaction was quenched with saturated ammonium chloride then diluted with ethyl acetate (50 mL), washed with 1N sodium hydroxide (3×30 mL) and saturated NaCl (10 mL), dried (MgSO$_4$) and evaporated at reduced pressure giving 21 as a brown film that was used without further purification.

Method Q; A mixture of 21 (1.04 mmol) and activated zinc metal (304 mg, 44.67 mmol) in acetic acid (5 mL) and the reaction was stirred at 80° C. for four hours. The reaction was filtered though celite, diluted with ethyl acetate (30 mL), washed with saturated sodium bicarbonate (3×25 mL) and saturated NaCl (5 mL), dried (MgSO$_4$) and evaporated at reduced pressure giving a brown foam. Chromatography (hexane/ether, 20 to 30%) gave a white powder. It was crystallized from dichloromethane giving 22 as colorless spikes, 41 mg (12% for two steps).

Method QQ; The n-butyllithium (1.3 mL, 2.1 mmol) was added to a solution of 21 (0.702 mmol) in tetrahydrofuran (5 mL) and the reaction was stirred for 5 minutes. Then the carbondisulfide (260 μL, 4.2 mmol) was added and the reaction was stirred for another 40 minutes. The reaction was diluted with ethyl acetate (30 mL), washed with 10% potassium carbonate (3×25 mL) and saturated NaCl (5 mL), dried (MgSO$_4$) and evaporated at reduced pressure giving a brown foam. Chromatography (hexane/ether, 20%) gave a colorless film. It was crystallized from cyclohexane giving 22 as colorless plates, 82 mg (34% for two steps).

Method R; A solution of 21 (0.520 mg) and 1,8-diazebicyclo[5.4.0]undec-7-ene (5 drops) in tetrahydrofuran (5 mL) was refluxed over night. The reaction was diluted with ethyl acetate (30 mL), washed with 1N HCl (2×25 mL), saturated sodium bicarbonate (25 mL) and saturated NaCl (5 mL), dried (MgSO$_4$) and evaporated at reduced pressure giving a yellow film. It was crystallized from dichloromethane and hexane giving 23 as a creamy white powder, 47 mg (26%).

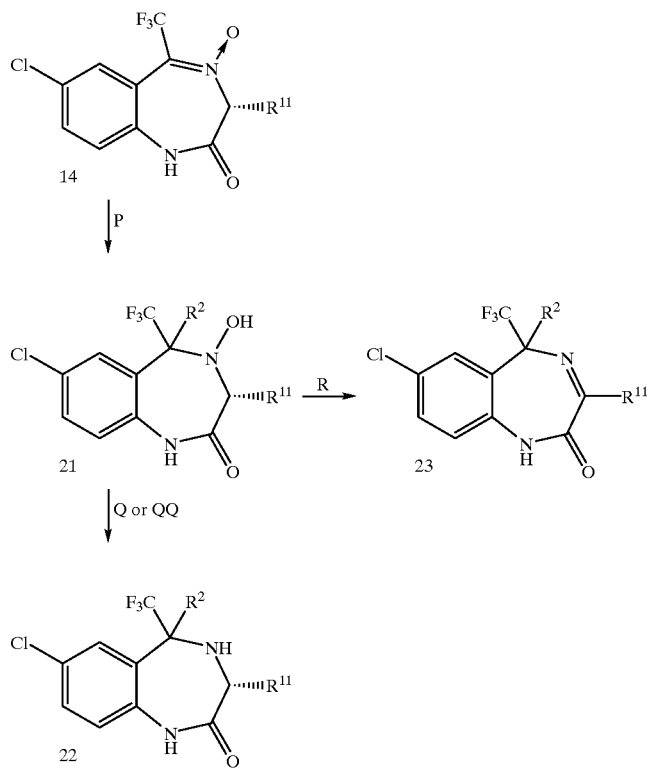

Example 7

Synnthesis of 5-substituted and 5-unsubstituted 1,4-benzodiaxepin-2-ones.

Method S; The titanium tetrachloride solution (236 μL, 2.15 mmol) was added dropwise to a solution of 1 (480 mg, 2.15 mmol), diisopropylethylamine (386 μL, 2.15 mmol) and aniline (392 μL, 4.30 mmol) in dichloromethane (10 mL) and the reaction was stirred for one hour. The reaction was diluted with ethyl acetate (30 mL), washed with 1N HCl (2×25 mL), saturated sodium bicarbonate (25 mL) and saturated NaCl (5 mL), dried (MgSO$_4$) and evaporated at reduced pressure giving a brown oil that was used without further purification.

Compound 28 was prepared using Method D and Method A. Compound 26 was prepared using Method L and Method A.

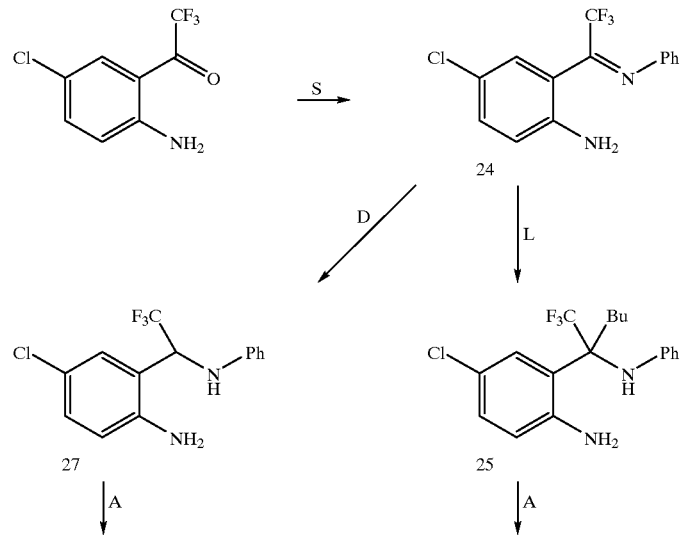

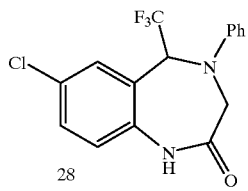 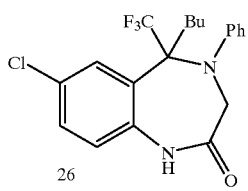

Example 8

Synthesis of substituted benzyl alcohols.

Method T; The 1.6 N n-butyl lithium (57.5 mL, 92.0 mmol) was slowly added to a chilled (−78° C.) solution of the substituted benzene (3-fluoroanisol, 10.5 g, 92.0 mmol) in tetrahydrofuran (100 mL) and the reaction was stirred for 30 minutes. Then N,N-dimethylformamide (7.83 mL, 101 mmol) was added and the reaction was allowed to warm to room temperature. After stirring for one hour at room temperature, the reaction was quenched with saturated ammonium chloride. The reaction was diluted with ethyl acetate (50 mL), washed saturated water (3×80 mL) and saturated NaCl (10 mL), dried (MgSO$_4$) and evaporated at reduced pressure giving a yellow paste. It was crystallized from hexane giving 25 as creamy white plates, 12.2 g (86%).

Method U; A solution of 25 (2-fluoro-6-methoxybenzaldehyde, 40.0 mmol) and excess sodium borohydride in methanol (30 mL) was stirred for 30 minutes. The reaction was diluted with ethyl acetate (30 mL), washed with 1N HCl (3×25 mL) and saturated NaCl (5 mL), dried (MgSO$_4$) and evaporated at reduced pressure giving 26 as a yellow oil that was used without further purification.

Method V; The methanesulfonyl chloride (3.70 g, 48.0 mmol) was added to a solution of 26 (40.0 mmol) and diisopropylethylamine (9.04 mL, 52.0 mmol) in dimethylformamide (30 mL) and the reaction was stirred for two hours. The reaction was diluted with ethyl acetate (50 mL), washed with 1N HCl (2×30 mL), saturated sodium bicarbonate (30 mL) and saturated NaCl (10 mL), dried (MgSO$_4$) and evaporated at reduced pressure giving an orange syrup. It was tricherated in hexane, decanted off an orange film and the hexane evaporated at reduced pressure giving 27 as a clear light yellow oil, 3.34 g (48%).

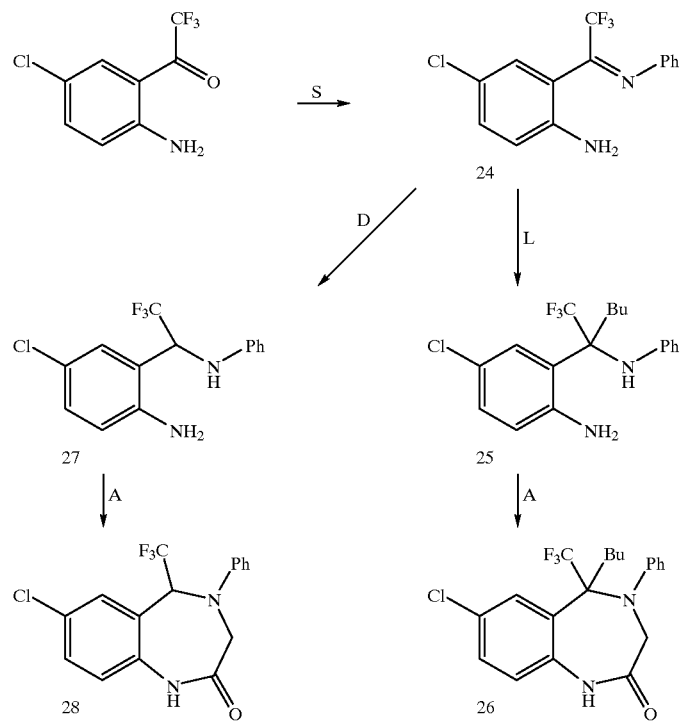

Example 9

Synthesis of organometallic acetylides.

Method W; The 1.6 N n-butyl lithium (3.82 mL, 6.11 mmol) was slowly added to a chilled (between −78° C. and 0° C.) solution of cyclopropylacetylene (6.88 mmol) in tetrahydrofuran (6 mL) and the reaction was stirred for 15 to 30 minutes giving a solution of 28.

Method X; The 2 N n-butylmagnesium chloride (1.50 mL, 3.00 mmol) was slowly added to a chilled (between 0° C. and room temperature) solution of cyclopropylacetylene (3.20 mmol) in tetrahydrofuran (6 mL) and the reaction was stirred for 30 minutes giving a solution of 29.

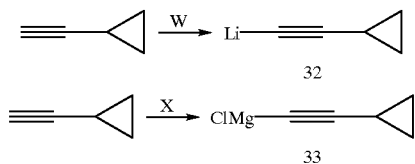

Example 10

Synthesis of substituted 4-(2-propynyl) substituted 1,4-benzodiazapin-2-ones.

Method a; A suspension of 5 (50 mg, 0.19 mmol) and hydroxymethyl benzotrizole (28 mg, 0.19 mmol) in toluene (1 mL) was refluxed overnight. The reaction was evaporated and dissolved in THF (2 mL). A solution of 33 in THF (4 mL, 1 mmol) was added and stirred overnight. The reaction was diluted with EtOAc, washed with saturated NH$_4$Cl and brine. Evaporated to give an orange glass (86 mg). Chromatography (30% EtOAc/hexane) gave a pale orange glass (20 mg) which was triturated with hexane and small amount ether to give pale orange solid 34 (9.8 mg).

Method a

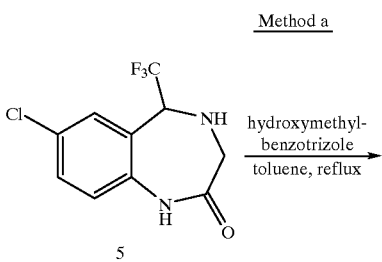

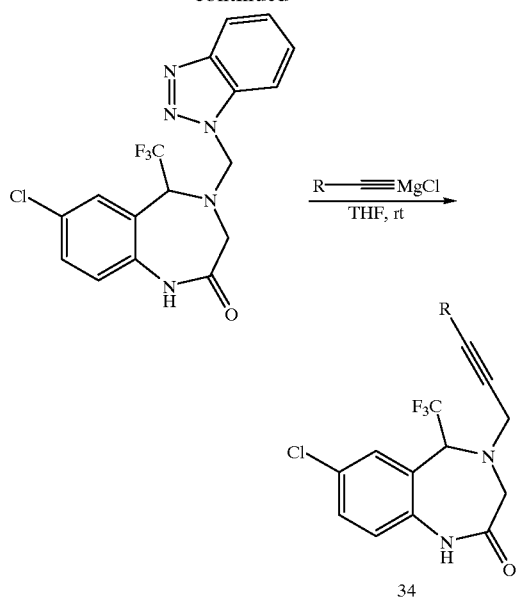

Example 11

Synthesis of 5-substitued 1,4-benzodiazapin-2-ones.

Method b; To a solution of 4 (50 mg, 0.19 mmol) in dichloroethane (2 mL) was added (Tf)$_2$O (100 uL, 0.58 mmol). The reaction precipitated. After stirred at room temperature for 4 h, the solvent was evaporated under nitrogen to give a pale yellow solid. To a −78° C. suspension the iminium salt 35 in ether (2 mL) was added a 2 M solution of BuMgCl in ether (150 uL). The reaction was quenched with saturated NH$_4$Cl, washed with saturated NH$_4$Cl and brine. Evaporated to give a yellow glass (85 mg). Chromatography (30% EtOAc/hexane) gave a colorlee glass (14 mg) which was triturated with hexane and ether to give white solid 36 (5.7 mg).

Method b

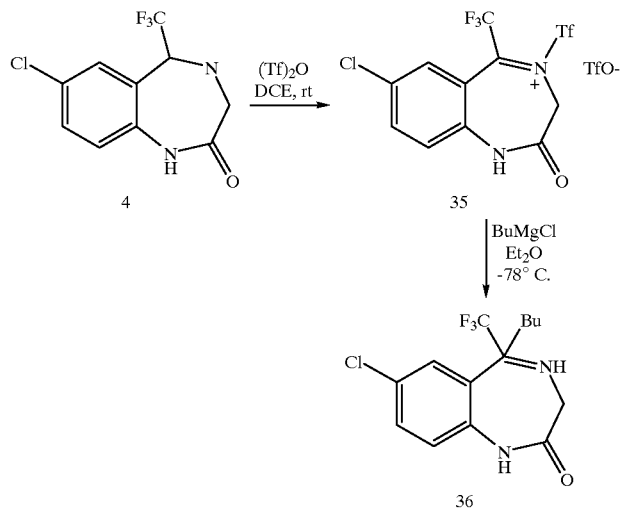

Example 12

Synthesis of 2-trifluoroacetyl-4-fluoroaniline.

Method c; To a 0° C. suspension of 37 (5 g, 25.6 mmol) in THF (100 mL) was added a 1.6M solution of BuLi in hexane (38.5 mL, 61.5 mmol) as a stream. The suspension dissolved and turned to gray color then changed to orange. After addition,, the reaction was stirred for 0.5 h and trifluro ethyl acetate (7.7 mL, 65 mmol). The reaction was followed by TLC and quenched with saturated NH$_4$Cl, washed with saturated NH$_4$Cl and brine. Dried over Na$_2$SO$_4$ evaporated to give a 38. A mixture of 38 in DME (20 mL) and 12N HCl (50 mL) was refluxed for 0.5 h. Cooled to room temperature. The reaction diluted with EtOAc, solid K$_2$CO$_3$ was added in small portions until pH >8, washed with brine. Dried over Na$_2$SO$_4$ and evaporated to give a crude orange oil. Chromatography (15% EtOAc/hexane) gave a orange oil 39 (3.2 g) which crystallized on stading.

Example 13

Synthesis of 6,7-Difluoro-5-(2-cyclopropyl-Z-ethenyl)-1,5-dihydro-5-(trifluoromethyl)-1,4-benzodiazepin-2-one.

Method d; To a refluxing solution of Rieke Zn in THF (6 mL) was added a solution of the acetylene 40 in MeOH (4 mL) and AcOH (0.4 mL) was refluxed for 48 h. The reaction was diluted with EtOAc, washed with saturated NaHCO$_3$ and brine. Evaporated to give a crude product (27 mg). Chromatography (2% MeOH/methylene chloride) gave a colorless glass which was crystallized from hexane to give a off-white solid 41 (5.2 mg).

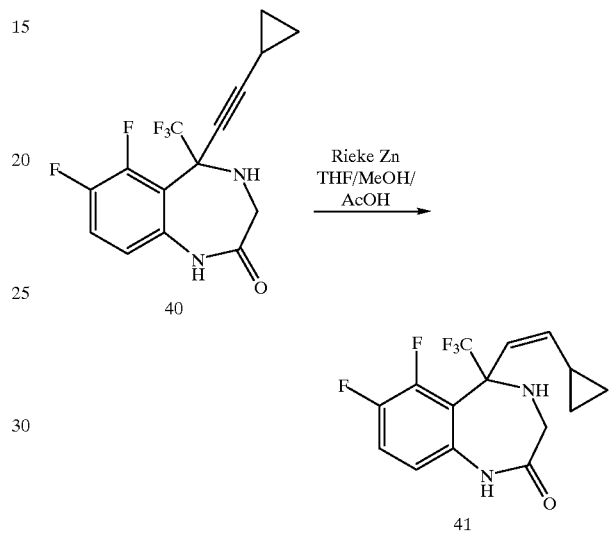

Method d

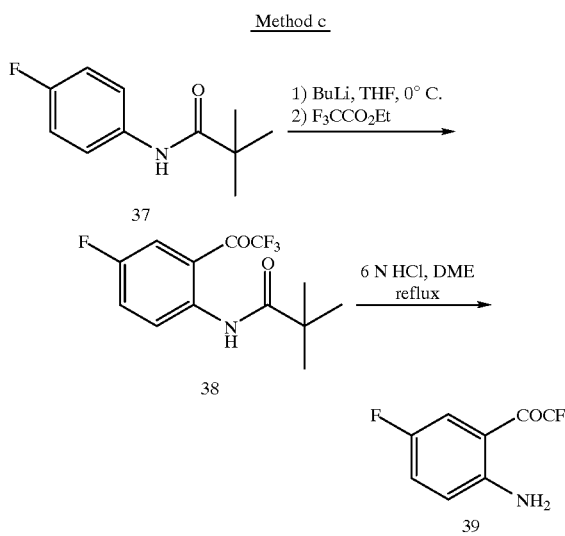

Method c

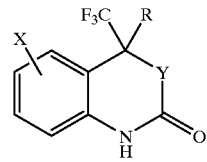

Table 1 below provides representative Examples of the compounds of Formula (I) of the present invention synthesized by the methods disclosed herein. Abbreviations used in Table 1 are defined as follows: "Bn" is benzyl; "Ph" is phenyl; "Py" is pyridyl; "iPr" is isopropyl; and "cycPr" is cyclopropyl.

TABLE 1

| Ex. # | X | R | Y = —N(R$^8$)—CH(R$^{11}$)— | Melting Pt (° C.) | Method |
|---|---|---|---|---|---|
| 100 | 7-Cl | H | N(Bu)CH$_2$ | 89–92 | AA,B,C,F,D,H |
| 101 | 7-Cl | H | N(CH$_2$CH=CMe$_2$)CH$_2$ | 120–125 | AA,B,C,D,G,H |
| 102 | 7-Cl | H | N(CH$_2$-2-Py)CH$_2$ | 184–187 | AA,B,C,D,G,H |
| 103 | 7-Cl | H | N(CH$_2$(2-Me-5-thiazolyl))CH$_2$ | 196–220 | AA,B,C,D,G,H |
| 104 | 7-Cl | H | N(CH$_2$(5-Me-2-Py))CH$_2$ | 200–205 | AA,B,C,D,G,H |
| 105 | 7-Cl | H | N(CH$_2$(6-Cl-2-Py))CH$_2$ | 184–186 | AA,B,C,D,G,H |
| 106 | 7-Cl | H | N(n-propyl)CH$_2$ | 123–124 | AA,B,C,D,EE |
| 107 | 7-Cl | H | N(n-hexyl)CH$_2$ | 87–88 | AA,B,C,D,EE |
| 108 | 7-Cl | H | N(n-pentyl)CH$_2$ | 114–115 | AA,B,C,D,EE |
| 109 | 7-Cl | H | N(C$_3$H$_6$Ph)CH$_2$ | 89–91 | AA,B,C,D,EE |
| 110 | 7-Cl | H | N(Bn)CH$_2$ | 142–143 | AA,B,C,D,G,H |
| 111 | 7-Cl | H | N(n-pentyl)CH$_2$ | 94–96 | AA,B,C,D,EE |
| 112 | 7-Cl | H | N(C$_3$H$_6$CH=CH$_2$)CH$_2$ | 84–85 | AA,B,C,D,EE |
| 113 | 7-Cl | H | N(2-CH$_3$—Bn)CH$_2$ | 197–198 | AA,B,C,D,G,H |

TABLE 1-continued

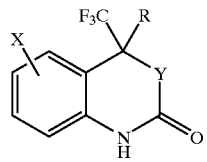

| Ex. # | X | R | Y = —N($R^8$)—CH($R^{11}$)— | Melting Pt (° C.) | Method |
|---|---|---|---|---|---|
| 114 | 7-Cl | H | N(2-Br—Bn)$CH_2$ | 161–162 | AA,B,C,D,G,H |
| 115 | 7-Cl | H | N(2-Cl-6-F—Bn)$CH_2$ | 171–172 | AA,B,C,D,G,H |
| 116 | 7-Cl | H | N(2-CN—Bn)$CH_2$ | 184–185 | AA,B,C,D,G,H |
| 117 | 7-Cl | H | N(2,6-diF-Bn)$CH_2$ | 173–174 | AA,B,C,D,G,H |
| 118 | 7-Cl | H | N(3-MeO—Bn)$CH_2$ | 171–172 | AA,B,C,D,G,H |
| 119 | 7-Cl | H | N(2,6-diCl-Bn)$CH_2$ | 190–191 | AA,B,C,D,G,H |
| 120 | 7-Ci | H | N(3-CN—Bn)$CH_2$ | 241–242 | AA,B,C,D,G,H |
| 121 | 7-Cl | H | N(2-MeO—Bn)$CH_2$ | 145–146 | AA,B,C,D,G,H |
| 122 | 7-Cl | H | N($CH_2$-2-thienyl)$CH_2$ | 105–107 | M,D,D |
| 123 | 7-Cl | H | N($CH_2$-3-thienyl)$CH_2$ | 148–150 | M,D,E |
| 124 | 7-Cl | H | N($CH_2$-2-furanyl)$CH_2$ | 143–145 | M,D,E |
| 125 | 7-Cl | H | N(3-Me-pentyl)$CH_2$ | 66–67 | M,D,E |
| 126 | 7-Cl | H | N($CH_2$(3-MeO-2-Py))$CH_2$ | 146–148 | M,F,D,E,H |
| 127 | 7-Cl | H | N($CH_2$C≡C-cycPr)$CH_2$ | 121–123 | M,D,a |
| 128 | 7-Cl | n-Bu | NH$CH_2$ | 121–123 | M,b |
| 129 | 7-Cl | H | N($CH_2$C≡C—Pr)$CH_2$ | 96–98 | M,D,a |
| 130 | 7-Cl | H | N($CH_2$C≡C-iPr)$CH_2$ | NA | M,D,a |
| 131 | 7-Cl | H | N(3-Me-pentyl)$CH_2$ | 113–116 | M,D,E |
| 132 | 6,7-diF | H | N(2-F-6-MeO-Bn)$CH_2$ | 168–170 | M,D,E |
| 133 | 6,7-diF | C≡C-ipr | N(OH)$CH_2$ | 174–176 | A,J,K,P |
| 134 | 7-Cl | C≡C-ipr | NH$CH_2$ | 185–187 | A,J,K,P,Q |
| 135 | 7-Cl | C≡C-2-thienyl | NH$CH_2$ | 196–198 | A,J,K,P,Q |
| 136 | 7-Cl | C≡C-iPr | N(n-Bu)$CH_2$ | 123–125 | A,J,K,P,Q,E |
| 137 | 7-Cl | H | N(2-F—Bn)$CH_2$ | 170–171 | AA,B,C,F,D,G,H |
| 138 | 7-Cl | H | N($CH_2CH_2$(2-Cl—Ph))$CH_2$ | 161–162 | AA,B,C,F,D,G,H |
| 139 | 7-Cl | H | N(benzoyl)$CH_2$ | 257–258 | AA,B,C,F,D,G,H |
| 140 | 7-Cl | H | N($CH_2CH_2$(2-I—Ph))$CH_2$ | 172–173 | AA,B,C,F,D,G,H |
| 141 | 7-Cl | H | N($CH_2CH_2$(3-Cl—Ph))$CH_2$ | 208–209 | AA,B,C,F,D,G,H |
| 142 | 7-Cl | H | N(3-F—Bn)$CH_2$ | 181–182 | AA,B,C,F,D,G,H |
| 143 | 7-Cl | H | N(2,6-diMeO-Bn)$CH_2$ | 128–129 | AA,B,C,F,D,T,U,V,G,H |
| 144 | 7-Cl | H | N(2,5-diMeO-Bn)$CH_2$ | 182–183 | AA,B,C,F,D,T,U,V,G,H |
| 145 | 7-Cl | H | N(2,5-diMeO-6-F—Bn)$CH_2$ | 121–122 | AA,B,C,F,D,T,U,V,G,H |
| 146 | 7-Cl | H | N(2-MeO-6-F—Bn)$CH_2$ | 107–108 | AA,B,C,F,D,T,U,V,G,H |
| 147 | 7-Cl | H | N(2,3-diF-Bn)$CH_2$ | 182–183 | A,B,C,F,D,G,H |
| 148 | 7-Cl | H | N(2,5-diF-Bn)$CH_2$ | 134–135 | A,B,C,F,D,G,H |
| 149 | 7-Cl | H | N($CH_2$C≡C$C_2H_5$)$CH_2$ | 123–124 | A,B,C,F,D,G,G,H |
| 150 | 7-Cl | H | N($CH_2$(4-Br-2-thienyl))$CH_2$ | 173–174 | M,D,E |
| 151 | 7-Cl | H | N($CH_2CH_2$-iPr)CHMe | 68–70 | M,D,E |
| 152 | 7-Cl | H | N($CH_2CH_2CH_2$CH=$CH_2$)$CH_2$ | 86–87 | M,D,E |
| 153 | 7-Cl | H | N($CH_2$CH=CH$C_2H_5$)$CH_2$ | 83–84 | M,D,E |
| 154 | 7-Cl | H | N($CH_2$C≡CPh)$CH_2$ | 138–139 | M,D,E |
| 155 | 7-Cl | H | N($CH_2$-4-(5-Cl-2,3-thiadiazole)$CH_2$ | 194–195 | AA,B,C,F,D,T,U,V,G,H |
| 156 | 7-Cl | H | N($CH_2$CH=CH-2-furanyl)$CH_2$ | 107–108 | M,D,E |
| 157 | 7-Cl | H | N(2,3-diF-6-OMe—Bn)$CH_2$ | 170–171 | AA,B,C,F,D,T,U,V,G, H |
| 158 | 7-Cl | H | N(2-F-6-OMe—Bn)$CH_2$ | 156–157 | M,D,E,Z |
| 159 | 7-Cl | Butyl | N(Ph)$CH_2$ | 177–178 | S,L,A |
| 160 | 7-Cl | H | N($CH_2$C≡CC$H_2CH_3$)$CH_2$ | 114–115 | M,D,G,Z |
| 161 | 7-Cl | C≡C-cycPr | NH$CH_2$ | 219–220 | M,W,P |
| 162 | 7-Cl | C≡C-cycPr | NH$CH_2$ | 213–214 | A,J,K,W,P,Q |
| 163 | 7-Cl | C≡C-cycPr | NH$CH_2$ | 215–216 | A,J,K,W,L |
| 164 | 7-Cl | H | N(Ph)$CH_2$ | 187–188 | S,D,A |
| 165 | 7-Cl | H | N($CH_2$C≡CH)$CH_2$ | 181–182 | M,D,G |
| 166 | 7-Cl | H | N($CH_2$C≡C$CH_3$)$CH_2$ | 174–175 | M,D,G |
| 167 | 7-Cl | $CH_2$C(=O)-cycPr | NH$CH_2$ | 148–149 | A,J,K,W,P,Q |
| 168 | 7-Cl | $CH_2$Ph | NH$CH_2$ | 160–161 | A,J,K,P,Q |
| 169 | 7-Cl | isobutyl | NH$CH_2$ | 118–119 | A,J,K,P,Q |
| 170 | 7-Cl | $CH_2CH_2$Ph | NH$CH_2$ | 182–183 | A,J,K,P,Q |

TABLE 1-continued

| Ex. # | X | R | Y = —N(R⁸)—CH(R¹¹)— | Melting Pt (° C.) | Method |
|---|---|---|---|---|---|
| 171 | 7-Cl | isopentyl | NHCH(CH₃) | 103–104 | A,J,K,P,Q |
| 172 | 7-Cl | C≡C-cycPr | NHCH(CH₃) | 171–172 | M,D,N,W,L |
| 173 | 7-Cl | C≡C-cycPr | NHCH₂ | 105–106 | M,D,N,W,L,Z |
| 174 | 7-Cl | α-C≡C-cycPr | NHCH₂ | 104–105 | M,D,N,W,L,Z |
| 175 | 7-Cl | C≡C-cycPr | N(Me)CH₂ | 135–136 | M,D,N,W,L,EE |
| 176 | 7-Cl | n-pentyl | NCH(isobutyl) | 94–95 | M,D,N,P,QQ |
| 177 | 7-Cl | C≡C-cycPr | NHCH(Me) | 164–165 | M,D,N,X,P,QQ |
| 178 | 7-Cl | C≡C-cycPr | NHCH(Me) | 165–166 | M,D,N,W,L,O |
| 179 | 7-Cl | n-pentyl | NHCH₂ | 142–143 | M,D,N,P,QQ |
| 180 | 7-Cl | H | N(CH₂(2-F-6Me-Ph))CH₂ | 196–197 | M,D,G,DD |
| 181 | H | n-pentyl | NHCH(Me) | 139–140 | M,D,N,P,QQ |
| 182 | 7-Cl | n-pentyl | N=C(i-Bu) | 113–114 | M,D,N,P,R |
| 183 | 7-Cl | C≡C-cycPr | NHCH(Me) | 138–139 | M,D,N,W,L |
| 184 | H | C≡C-cycPr | NHCH α-(Me) | 168–169 | M,DD,N,W,L |
| 185 | H | C≡C-cycPr | NHCH β-(Me) | 198–199 | M,DD,N,W,L,O |
| 186 | H | C≡C-cycPr | NHCH(Et) | 181–182 | M,D,N,W,L,O |
| 187 | 7-Cl | n-pentyl | NHCH₂ | 153–155 | A,J,K,P,Q |
| 188 | 7-Cl | isopentyl | NHCH₂ | 150–152 | A,J,K,P,Q |
| 189 | 7-Cl | isopentyl | NHCH₂ | 151–153 | A,J,K,P,Q |
| 190 | 7-Cl | CH₂Ph | NHCH₂ | 160–162 | A,J,K,P,Q |
| 191 | 7-Cl | CH=CH-cycPr (trans) | NHCH₂ | 150–153 | A,J,K,P,Q |
| 192 | 7-Cl | n-hexyl | NHCH₂ | 115–120 | A,J,K,P,Q |
| 193 | 7-Cl | CH₂CH₂-cycPr | NHCH₂ | 152–155 | A,J,K,P,Q |
| 194 | 7-Cl | CH₂CH₂-cycPr | NHCH(Me) | 146–148 | M,D,N,P,Q |
| 195 | 6,7-diF | C≡C-cycPr | NHCH₂ | 185–187 | A,B,C,D,N,L |
| 196 | 7-Cl | CH₂-cycPr | NHCH₂ | 105–108 | A,J,K,P,Q |
| 197 | 7-Cl | —(CH₂)₃CF₃ | NHCH₂ | 178–180 | A,J,K,P,Q |
| 198 | 7-MeO | C≡C-cycPr | NHCH₂ | 145–146 | A,J,K,L |
| 199 | 7-F | C≡C-cycPr | NHCH₂ | 175–178 | C,M,D,N,L |
| 200 | 7-F | CH=CH-cycPr (cis) | NHCH₂ | 158–160 | A,B,C,D,N,L,d |
| 201 | 6,7-diF | CH₂CH₂CF₃ | NHCH₂ | 160–163 | A,J,K,P,Q |
| 202 | 7-Cl | CH₂-2-Py | NHCH₂ | 137–140 | A,J,K,P,Q |
| 203 | 7-Cl | n-Bu | NHCH₂ | 174–176 | A,J,K,P,Q |

*Unless otherwise noted, stereochemistry is (+/−) and in R² all double bonds are cis and trans.

Utility

The compounds of this invention possess reverse transcriptase inhibitory activity, in particular, HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

Compounds tested in the assay described below are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described below, a number of compounds of the present invention were found to exhibit a $K_i$ of $\leq 10$ μM, thereby confirming the utility of the compounds of the present invention as effective HIV reverse transcriptase inhibitors.

HIV RNA Assay

DNA Plasmids and in vitro RNA Transcripts:

Plasmid pDAB 72 containing both gag and pol sequences of BH10 (bp 113-1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at $-70°$ C. The concentration of RNA was determined from the $A_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 μM stocks in 2×SSC (0.3 M NaCl, 0.03 M sodium citrate), 0.05 M Tris pH 8.8, 1 mg/mL BSA. The biotinylated capture probes were prepared as 100 μM stocks in water.

Streptavidin Coated Plates:

Streptavidin coated plates were obtained from Du Pont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 μg/mL gentamycin, all from Gibco. HIV-1 RF was propagated in MT-4 cells in the same medium. Virus stocks were prepared approximately 10 days after acute infection of MT-4 cells and stored as aliquots at $-70°$ C. Infectious titers of HIV-1 (RF) stocks were $1-3\times10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 μL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 μl of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 μL of 0.2 mM 4-methylumbelliferyl phosphate (MUBP, JBL Scientific) in buffer δ (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 μL) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 μL) was added to culture wells containing cells and dilutions of the test compounds. The final volume in each well was 200 μL. Eight wells per plate were left uninfected with 50 μL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 μL of medium/well was removed from the HIV infected plates. Thirty seven μL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~$3 \times 10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of PDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection. A compound was considered active if its $IC_{90}$ was found to be less than 20 μM.

For antiviral potency tests, all manipulations in microtiter plates, following the initial addition of 2x concentrated compound solution to a single row of wells, were performed using a Perkin Elmer/Cetus ProPette.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the $IC_{90}$. The fold increase in apparent $IC_{90}$ for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the $IC_{90}$. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed is:
1. A compound of Formula (I):

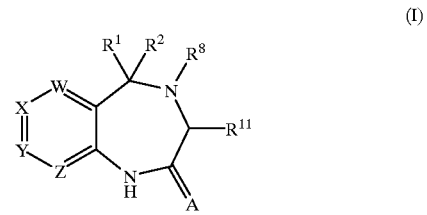

or a stereoisomer or pharmaceutically acceptable salt form thereof, wherein:

A is O or S;

W is $CR^3$;

X is $CR^{3a}$;

Y is $CR^{3b}$;

Z is $CR^{3c}$;

$R^1$ is selected from the group cyclopropyl and $C_{1-3}$ alkyl substituted with 0–7 halogen;

$R^2$ is selected from the group H, —$R^{2c}$, —$CH_2C(=O)R^{2c}$, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C=C—R^{2b}$, —$OCHR^{2a}C=R^{2c}$, —$OCHR^{2a}C≡C—R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C=C—R^{2b}$, —$SCHR^{2a}C=R^{2c}$, —$SCHR^{2a}C≡C—R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C=C—R^{2b}$, —$NHCHR^{2a}C=R^{2c}$, and —$NHCHR^{2a}C≡C—R^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group $C_{1-6}$ alkyl substituted with 0–2 $R^4$; $C_{2-5}$ alkenyl substituted with 0–2 $R^4$; $C_{2-5}$ alkynyl substituted with 0–1 $R^4$; $C_{3-6}$ cycloalkyl substituted with 0–2 $R^{3d}$; phenyl substituted with 0–2 $R^{3d}$; and 3–6 membered heterocyclic system containing 1–3 heteroatoms selected from the group O, N, and S, substituted with 0–2 $R^{3d}$;

alternatively, the group —$NR^{2a}R^{2c}$ represents a 4–7 membered cyclic amine, wherein 0–1 carbon atoms are replaced by O or $NR^5$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^4$ is selected from the group F, Cl, Br, I, CF$_3$, C$_{1-6}$ alkyl substituted with 0–2 R$^{3e}$; C$_{3-10}$ carbocycle substituted with 0–2 R$^{3e}$; phenyl substituted with 0–5 R$^{3e}$; and a 5–10 membered heterocyclic system containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group C$_{1-3}$ alkyl and C$_{1-3}$ alkoxy;

R$^8$ is selected from the group H, OH, C$_{1-6}$ alkyl substituted with 0–2 R$^9$; C$_{2-6}$ alkenyl substituted with 0–2 R$^9$; C$_{2-6}$ alkynyl substituted with 0–2 R$^9$; C$_{3-5}$ cycloalkyl substituted with 0–2 R$^{3f}$; phenyl substituted with 0–5 R$^{3f}$; and a 5–6 membered heterocyclic system containing 1–3 heteroatoms selected from the group O, N, and S, substituted with 0–2 R$^{3f}$;

R$^9$ is selected from the group benzoyl; C$_{3-10}$ carbocycle substituted with 0–5 R$^{3f}$; and a 5–10 membered heterocyclic system containing 1–3 heteroatoms selected from the group O, N, and S, substituted with 0–2 R$^{3f}$;

R$^{10}$ is selected from the group C$_{1-4}$ alkyl and phenyl; and

R$^{11}$ is selected from the group H, C$_{1-6}$ alkyl, C$_{1-6}$ alkenyl, C$_{1-6}$ alkynyl, aralkyl, aryl.

2. A compound according to claim 1, wherein:

A is O;

W is CR$^3$;

X is CR$^{3a}$;

Y is CR$^{3b}$;

Z is CH;

R$^1$ is selected from the group cyclopropyl and C$_{1-3}$ alkyl substituted with 1–7 halogen;

R$^2$ is selected from the group H, —R$^{2c}$, —CH$_2$C(=O)R$^{2c}$, —OR$^{2c}$, —OCHR$^{2a}$R$^{2b}$, —OCH$_2$CHR$^{2a}$R$^{2b}$, —(CH$_2$)$_2$CHR$^{2a}$R$^{2b}$, —OCHR$^{2a}$C=C—R$^{2b}$, OCHR$^{2a}$C=R$^{2c}$, and —OCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-5}$ alkyl substituted with 0–2 R$^4$; C$_{2-5}$ alkenyl substituted with 0–2 R$^4$; C$_{2-5}$ alkynyl substituted with 0–1 R$^4$; C$_{3-6}$ cycloalkyl substituted with 0–2 R$^{3d}$; and phenyl substituted with 0–2 R$^{3d}$;

R$^3$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

R$^{3a}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$, at each occurrence, is independently selected from the group H, C$_{1-3}$ alkyl, OH, C$_{1-3}$ alkoxy, F, and Cl;

alternatively, R$^{3a}$ and R$^{3b}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^4$ is selected from the group Cl, F, CF$_3$; C$_{1-4}$ alkyl substituted with 0–2 R$^{3e}$; C$_{3-5}$ carbocycle substituted with 0–2 R$^{3e}$; phenyl substituted with 0–5 R$^{3e}$; and a 5–6 membered heterocyclic system containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, CH(CH$_3$)$_2$, OCH$_3$, OC$_2$H$_5$, and OCH(CH$_3$)$_2$; and, R$^8$ is selected from the group H, OH; C$_{1-6}$ alkyl substituted with 0–2 R$^9$; C$_{2-6}$ alkenyl substituted with 0–2 R$^9$; C$_{2-6}$ alkynyl substituted with 0–2 R$^9$; C$_{3-5}$ cycloalkyl substituted with 0–2 R$^{3f}$; phenyl substituted with 0–5 R$^{3f}$; and a 5–6 membered heterocyclic system containing 1–3 heteroatoms selected from the group O, N, and S, substituted with 0–2 R$^{3f}$;

R$^9$ is selected from the group benzoyl; C$_{3-10}$ carbocycle substituted with 0–5 R$^{3f}$; and a 5–10 membered heterocyclic system containing 1–3 heteroatoms selected from the group O, N, and S, substituted with 0–2 R$^{3f}$;

R$^{11}$ is selected from the group H, cyclopropyl, CH$_3$, C$_2$H$_5$, and CH(CH$_3$)$_2$, n-propyl, n-butyl, iso-butyl.

3. A compound according to claim 2, wherein:

A is O;

W is CR$^3$;

X is CR$^{3a}$;

Y is CH;

Z is CH;

$R^1$ is selected from the group $CHF_2$, $CF_3$, and $C_2F_5$;

$R^2$ is selected from the group H, —$R^{2c}$, —$CH_2C(=O)R^{2c}$, —$OCH_2R^{2b}$, —$OCH_2CH_2R^{2b}$, —$OCH_2C=C—R^{2b}$, and —$OCH_2C\equiv C—R^{2b}$;

$R^{2b}$ is H or $R^{2c}$;

$R^{2c}$ is selected from the group $C_{1-4}$ alkyl substituted with 0–2 $R^4$; $C_{2-3}$ alkenyl substituted with 0–2 $R^4$; $C_{2-3}$ alkynyl substituted with 0–1 $R^4$; and $C_{3-6}$ cycloalkyl substituted with 0–2 $R^{3d}$;

$R^3$, at each occurrence, is independently selected from the group H, $C_{1-3}$ alkyl, OH, $C_{1-3}$ alkoxy, F, Cl, Br, $NR^5R^{5a}$, $NO_2$, —CN, $C(O)R^6$, $NHC(O)R^7$, and $NHC(O)NR^5R^{5a}$;

$R^{3a}$, at each occurrence, is independently selected from the group H, $C_{1-3}$ alkyl, OH, $C_{1-3}$ alkoxy, F, Cl, Br, $NR^5R^{5a}$, $NO_2$, —CN, $C(O)R^6$, $NHC(O)R^7$, and $NHC(O)NR^5R^{5a}$;

alternatively, $R^3$ and $R^{3a}$ together form —$OCH_2O$—;

$R^{3e}$, at each occurrence, is independently selected from the group H, $C_{1-4}$ alkyl, —OH, $C_{1-4}$ alkoxy, $OCF_3$, F, Cl, —$NR^5R^{5a}$, —$C(O)R^6$, and —$SO_2NR^5R^{5a}$;

$R^{3f}$, at each occurrence, is independently selected from the group H, $C_{1-4}$ alkyl, —OH, $C_{1-4}$ alkoxy, $OCF_3$, F, Cl, —$NR^5R^{5a}$, —$C(O)R^6$, and —$SO_2NR^5R^{5a}$;

$R^4$ is selected from the group Cl, F, $CF_3$, $C_{1-4}$ alkyl substituted with 0–1 $R^{3e}$; $C_{3-5}$ carbocycle substituted with 0–2 $R^{3e}$; phenyl substituted with 0–2 $R^{3e}$; and a 5–6 membered heterocyclic system containing 1–3 heteroatoms selected from the group O, N, and S, substituted with 0–1 $R^{3e}$;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; and, $R^8$ is selected from the group H, OH; $C_{1-6}$ alkyl substituted with 0–2 $R^9$; $C_{2-6}$ alkenyl substituted with 0–2 $R^9$; $C_{2-6}$ alkynyl substituted with 0–2 $R^9$; $C_{3-5}$ cycloalkyl substituted with 0–2 $R^{3f}$; phenyl substituted with 0–5 $R^{3f}$; and a 5–6 membered heterocyclic system containing 1–3 heteroatoms selected from the group O, N, and S, substituted with 0–2 $R^{3f}$;

$R^9$ is selected from the group benzoyl; $C_{3-6}$ carbocycle substituted with 0–5 $R^{3f}$; and a 5–6 membered heterocyclic system containing 1–3 heteroatoms selected from the group O, N, and S, substituted with 0–2 $R^{3f}$;

$R^{11}$ is selected from the group H, cyclopropyl, $CH_3$, $C_2H_5$, and $CH(CH_3)_2$, n-propyl, n-butyl, iso-butyl.

4. A compound according to claim 3, wherein:

A is O;

W is $CR^3$;

X is $CR^{3a}$;

Y is CH;

Z is CH;

$R^1$ is $CF_3$;

$R^2$ is selected from the group H, $R^{2c}$ and $CH_2C(=O)R^{2c}$;

$R^{2c}$ is selected from the group $C_{1-4}$ alkyl substituted with 1 $R^4$; $C_{2-3}$ alkenyl substituted with 1 $R^4$; and $C_{2-3}$ alkynyl substituted with 1 $R^4$;

$R^3$, at each occurrence, is independently selected from the group H, methyl, ethyl, OH, methoxy, ethoxy, F, and Cl;

$R^{3a}$, at each occurrence, is independently selected from the group H, methyl, ethyl, OH, methoxy, ethoxy, F, and Cl;

alternatively, $R^3$ and $R^{3a}$ together form —$OCH_2O$—;

$R^{3e}$, at each occurrence, is independently selected from the group H, methyl, ethyl, OH, methoxy, ethoxy, F, and Cl;

$R^{3f}$, at each occurrence, is independently selected from the group H, methyl, ethyl, OH, methoxy, ethoxy, F, and Cl;

$R^4$ is selected from the group Cl, F, $CF_3$, $CH_3$, $CH_2CH_3$, $CH(CH_3)_2$; cyclopropyl-substituted with 0–1 $R^{3e}$; 1-methyl-cyclopropyl-substituted with 0–1 $R^{3e}$; cyclobutyl substituted with 0–1 $R^{3e}$; phenyl substituted with 0–2 $R^{3e}$; and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

$R^5$ and $R^{5a}$ are independently selected from the group H, $CH_3$ and $C_2H_5$;

$R^8$ is selected from the group H, OH; $C_{1-6}$ alkyl substituted with 0–1 $R^9$; $C_{2-6}$ alkenyl substituted with 0–1 $R^9$; $C_{2-6}$ alkynyl substituted with 0–1 $R^9$; $C_{3-5}$ cycloalkyl substituted with 0–2 $R^{3f}$; and phenyl substituted with 0–5 $R^{3f}$;

$R^9$ is selected from the group benzoyl; $C_{3-6}$ cycloalkyl substituted with 0–3 $R^{3f}$; and a $C_{3-6}$ phenyl substituted with 0–3 $R^{3f}$; and a 5–6 membered heterocyclic system containing 1–3 heteroatoms selected from the group O, N, and S, substituted with 0–2 $R^{3f}$; wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl; and $R^{11}$ is selected from the group H, cyclopropyl, $CH_3$, $C_2H_5$, and $CH(CH_3)_2$, n-propyl, n-butyl, iso-butyl.

5. A compound of claim 1 wherein:

A is O;

W is $CR^3$;

X is $CR^{3a}$;

Y is CH;

Z is CH;

$R^1$ is $CF_3$;

$R^3$ is H, F, Cl, methyl, or methoxy;

$R^{3a}$ is H, F, Cl, methyl, or methoxy;

$R^2$ is H, methyl-, ethyl-, propyl-, butyl-, pentyl-, hexyl-, $CF_3CH_2CH_2$—, $CF_3CH_2CH_2CH_2$—, $PhCH_2$—, $PhCH_2CH_2$—, cycPr—$CH_2$—, cycPr—$CH_2CH_2$—, pyrid-2-yl-$CH_2$—, cycPr—$C(=O)CH_2$—, cycPr—CH=CH—, iPr—$C\equiv C$—, cycPr—$C\equiv C$—, or thien-2-yl-$C\equiv C$—;

$R^8$ is H, OH, methyl, ethyl, n-propyl, i-propyl, n-butyl, n-hexyl, n-pentyl, 3-$CH_3$-pentyl, $(CH_3)_2CHCH_2CH_2$—, —$CH_2CH=C(CH_3)_2$, —$CH_2CH_2CH_2CH=CH_2$, —$CH_2CH=CHC_2H_5$, —$CH_2C\equiv CH$, —$CH_2C\equiv CCH_3$, —$CH_2C\equiv C$—cycPr, —$CH_2C\equiv C$—$CH_2CH_2CH_3$, —$CH_2C\equiv CCH_2CH_3$, —$CH_2C\equiv C$-isopropyl, —$CH_2C\equiv C$-phenyl, -phenyl, —$CH_2CH_2$-phenyl, —$CH_2CH_2CH_2$-phenyl, —$CH_2(2$-F-6-$CH_3$-phenyl), —$CH_2CH_2(2$-Cl-phenyl), —$CH_2CH_2(2$-I-phenyl), —CH₂CH₂(3-Cl-phenyl), benzyl-, 2-CH₃-benzyl-, 2-F-benzyl-, 2-Cl-benzyl-, 2-Br-benzyl-, 2-MeO-benzyl-, 2-CN-benzyl-, 3-F-benzyl-, 3-Cl-benzyl-, 3-MeO-benzyl-, 3-CN-benzyl-, 2,3-diF-benzyl-, 2,4-diF-benzyl-, 2,5-diF-benzyl-, 2,6-diF-benzyl-, 2,6-diCl-benzyl-, 2-Cl-6-F-benzyl-, 2-F-6-MeO-benzyl-, 2,6-diMeO-benzyl-, 2,5-diMeO-benzyl-, 2-MeO-6-F-benzyl-, 2,5-diMeO-6-F-benzyl-, 2,3-diF-6-MeO-benzyl-, benzoyl-, —CH₂-pyrid-2-yl, —CH₂(2-Me-thiazol-5-yl), —CH₂(5-Me-pyrid-2-yl), —CH₂(6-Cl-pyrid-2-yl), —CH₂-thien-2-yl, —CH₂-thien-3-yl, —CH₂(4-Br-thien-2-yl), —CH₂-furan-2-yl, —CH₂CH=CH-furan-2-yl, —CH₂(3-MeO-pyrid-2-yl), and —CH₂-(5-Cl-2,3-thiadiazol-4-yl); and $R^{11}$ is H, cyclopropyl, $CH_3$, $C_2H_5$, $CH(CH_3)_2$, n-propyl, n-butyl, or iso-butyl.

6. A compound of claim 1 wherein the compound is of Formula (Ic):

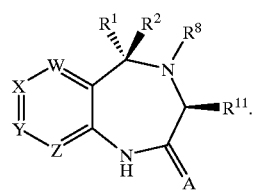

7. A compound of claim 1 wherein the compound is of Formula (Id):

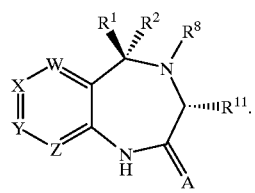

8. A compound of claim 1 wherein the compound is of Formula (Ie):

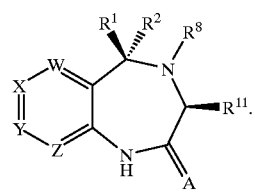

9. A compound of claim 1 wherein the compound is of Formula (If):

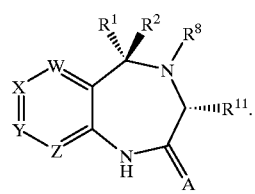

10. The compound according to claim 1, wherein the compound is selected from the group:

7-Chloro-4-butyl-1,5-dihydro-5-(trifluoromethyl)-1,4-benzodiazepin-2-one;

7-Chloro-4-(3-methyl-2-butenyl)-1,5-dihydro-5-(trifluoromethyl)-1,4-benzodiazepin-2-one;

7-Chloro-4-(2-pyridylmethyl)-1,5-dihydro-5-(trifluoromethyl)-1,4-benzodiazepin-2-one;

7-Chloro-4-(2-methyl-5-thiazolylmethyl)-1,5-dihydro-5-(trifluoromethyl)-1,4-benzodiazepin-2-one; and 7-Chloro-4-(5-methyl-2-pyridylmethyl)-1,5-dihydro-5-(trifluoromethyl)-1,4-benzodiazepin-2-one;

or a pharmaceutically acceptable salt form thereof.

11. A pharmaceutical composition, comprising: a pharmaceutically acceptable carrier and a therapeutically effective amount of a compound of claim 1 or pharmaceutically acceptable salt form thereof.

12. A method for treating HIV infection, comprising: administering to a host in need of such treatment a therapeutically effective amount of a compound of claim 1 or pharmaceutically acceptable salt form thereof.

13. The compound according to claim 1, wherein the compound is selected from the group:

7-Chloro-4-(6-chloro-2-pyridylmethyl)-1,5-dihydro-5-(trifluoromethyl)-1,4-benzodiazepin-2-one;

7-Chloro-4-propyl-1,5-dihydro-5-(trifluoromethyl)-1,4-benzodiazepin-2-one;

7-Chloro-4-hexyl-1,5-dihydro-5-(trifluoromethyl)-1,4-benzodiazepin-2-one;

7-Chloro-4-pentyl-1,5-dihydro-5-(trifluoromethyl)-1,4-benzodiazepin-2-one;

7-Chloro-4-(3-phenylpropyl)-1,5-dihydro-5-(trifluoromethyl)-1,4-benzodiazepin-2-one;

or a pharmaceutically acceptable salt form thereof.

14. The compound according to claim 1, wherein the compound is selected from the group:

7-Chloro-4-benzyl-1,5-dihydro-5-(trifluoromethyl)-1,4-benzodiazepin-2-one;

7-Chloro-4-pentyl-1,5-dihydro-5-(trifluoromethyl)-1,4-benzodiazepin-2-one;

7-Chloro-4-(5-pentenyl)-1,5-dihydro-5-(trifluoromethyl)-1,4-benzodiazepin-2-one;

7-Chloro-4-(2-methylbenzyl)-1,5-dihydro-5-(trifluoromethyl)-1,4-benzodiazepin-2-one;

7-Chloro-4-(2-bromobenzyl)-1,5-dihydro-5-(trifluoromethyl)-1,4-benzodiazepin-2-one;

or a pharmaceutically acceptable salt form thereof.

15. The compound according to claim 1, wherein the compound is selected from the group:

7-Chloro-4-(2-chloro-6-fluorobenzyl)-1,5-dihydro-5-(trifluoromethyl)-1,4-benzodiazepin-2-one;

7-Chloro-4-(2-cyanobenzyl)-1,5-dihydro-5-(trifluoromethyl)-1,4-benzodiazepin-2-one;

7-Chloro-4-(2,6-difluorobenzyl)-1,5-dihydro-5-(trifluoromethyl)-1,4-benzodiazepin-2-one;

7-Chloro-4-(3-methoxybenzyl)-1,5-dihydro-5-(trifluoromethyl)-1,4-benzodiazepin-2-one;

7-Cloro-4-(2,6-diclorobenzyl)-1,5-dihydro-5-(trifluoromethyl)-1,4-benzodiazepin-2-one;

or a pharmaceutically acceptable salt form thereof.

16. The compound according to claim 1, wherein the compound is selected from the group:

7-Chloro-4-(3-cyanobenzyl)-1,5-dihydro-5-(trifluoromethyl)-1,4-benzodiazepin-2-one;

7-Chloro-4-(2-methoxybenzyl)-1,5-dihydro-5-(trifluoromethyl)-1,4-benzodiazepin-2-one;

7-Chloro-4-(2-thienylmethyl)-1,5-dihydro-5-(trifluoromethyl)-1,4-benzodiazepin-2-one;

7-Chloro-4-(3-thienylmethyl)-1,5-dihydro-5-(trifluoromethyl)-1,4-benzodiazepin-2-one;

7-Chloro-4-(2-furanylmethyl)-1,5-dihydro-5-(trifluoromethyl)-1,4-benzodiazepin-2-one;

or a pharmaceutically acceptable salt form thereof.

17. The compound according to claim 1, wherein the compound is selected from the group:

7-Chloro-4-(3-methylpentyl)-1,5-dihydro-5-(trifluoromethyl)-1,4-benzodiazepin-2-one;

7-Chloro-4-(3-methoxy-2-pyridylmethyl)-1,5-dihydro-5-(trifluoromethyl)-1,4-benzodiazepin-2-one;

7-Chloro-4-(3-cyclopropyl-2-propynyl)-1,5-dihydro-5-(trifluoromethyl)-1,4-benzodiazepin-2-one;

7-Chloro-5-butyl-1,5-dihydro-5-(trifluoromethyl)-1,4-benzodiazepin-2-one;

7-Chloro-4-(2-hexynyl)-1,5-dihydro-5-(trifluoromethyl)-1,4-benzodiazepin-2-one;

or a pharmaceutically acceptable salt form thereof.

18. The compound according to claim 1, wherein the compound is selected from the group:

7-Chloro-4-(4-methyl-2-pentynyl)-1,5-dihydro-5-(trifluoromethyl)-1,4-benzodiazepin-2-one;

7-Chloro-4-(3-methylpentyl)-1,5-dihydro-5-(trifluoromethyl)-1,4-benzodiazepin-2-one;

6,7-Difluoro-4-(2-fluoro-6-methoxybenzyl)-1,5-dihydro-5-(trifluoromethyl)-1,4-benzodiazepin-2-one;

6,7-Difluoro-4-hydroxy-5-(3-methyl-1-butynyl)-1,5-dihydro-5-(trifluoromethyl)-1,4-benzodiazepin-2-one;

7-Chloro-5-(3-methyl-1-butynyl)-1,5-dihydro-5-(trifluoromethyl)-1,4-benzodiazepin-2-one;

or a pharmaceutically acceptable salt form thereof.

19. The compound according to claim 1, wherein the compound is selected from the group:

7-Chloro-5-(2-thienylethynyl)-1,5-dihydro-5-(trifluoromethyl)-1,4-benzodiazepin-2-one;

7-Chloro-4-butyl-5-(3-methyl-1-butynyl)-1,5-dihydro-5-(trifluoromethyl)-1,4-benzodiazepin-2-one;

7-Chloro-4-(2-fluorobenzyl)-1,5-dihydro-5-(trifluoromethyl)-1,4-benzodiazepin-2-one;

7-Chloro-4-(2-(2-chlorophenyl)ethyl)-1,5-dihydro-5-(trifluoromethyl)-1,4-benzodiazepin-2-one;

7-Chloro-4-benzoyl-1,5-dihydro-5-(trifluoromethyl)-1,4-benzodiazepin-2-one;

or a pharmaceutically acceptable salt form thereof.

20. The compound according to claim 1, wherein the compound is selected from the group:

7-Chloro-4-(2-(2-iodophenyl)ethyl)-1,5-dihydro-5-(trifluoromethyl)-1,4-benzodiazepin-2-one;

7-Chloro-4-(2-(3-chlorophenyl)ethyl)-1,5-dihydro-5-(trifluoromethyl)-1,4-benzodiazepin-2-one;

7-Chloro-4-(3-fluorobenzyl)-1,5-dihydro-5-(trifluoromethyl)-1,4-benzodiazepin-2-one;

7-Chloro-4-(2,6-dimethoxybenzyl)-1,5-dihydro-5-(trifluoromethyl)-1,4-benzodiazepin-2-one;

7-Chloro-4-(2,5-dimethoxybenzyl)-1,5-dihydro-5-(trifluoromethyl)-1,4-benzodiazepin-2-one;

or a pharmaceutically acceptable salt form thereof.

21. The compound according to claim 1, wherein the compound is selected from the group:

7-Chloro-4-(2,5-dimethoxy-6-fluorobenzyl)-1,5-dihydro-5-(trifluoromethyl)-1,4-benzodiazepin-2-one;

7-Chloro-4-(2-methoxy-6-fluorobenzyl)-1,5-dihydro-5-(trifluoromethyl)-1,4-benzodiazepin-2-one;

7-Chloro-4-(2,3-difluorobenzyl)-1,5-dihydro-5-(trifluoromethyl)-1,4-benzodiazepin-2-one;

7-Chloro-4-(2,5-difluorobenzyl)-1,5-dihydro-5-(trifluoromethyl)-1,4-benzodiazepin-2-one;

7-Chloro-4-(2-pentynyl)-1,5-dihydro-5-(trifluoromethyl)-1,4-benzodiazepin-2-one;

or a pharmaceutically acceptable salt form thereof.

22. The compound according to claim 1, wherein the compound is selected from the group:

7-Chloro-4-(4-bromothien-2-ylmethyl)-1,5-dihydro-5-(trifluoromethyl)-1,4-benzodiazepin-2-one;

7-Chloro-4-(3-methylbutyl)-1,5-dihydro-5-(trifluoromethyl)-1,4-benzodiazepin-2-one;

7-Chloro-4-(4-penten-1-yl)-1,5-dihydro-5-(trifluoromethyl)-1,4-benzodiazepin-2-one;

7-Chloro-4-(2-penten-1-yl)-1,5-dihydro-5-(trifluoromethyl)-1,4-benzodiazepin-2-one;

7-Chloro-4-(3-phenyl-2-propynyl)-1,5-dihydro-5-(trifluoromethyl)-1,4-benzodiazepin-2-one;

or a pharmaceutically acceptable salt form thereof.

23. The compound according to claim 1, wherein the compound is selected from the group:

7-Chloro-4-(4-(5-chloro-2,3-thiadiazole)methyl)-1,5-dihydro-5-(trifluoromethyl)-1,4-benzodiazepin-2-one;

7-Chloro-4-(3-(2-furanyl)-2-propenyl)-1,5,-dihydro-5-(trifluoromethyl)-1,4-benzodiazepin-2-one;

7-Chloro-4-(2,3-difluoro-6-methoxybenzyl)-1,5-dihydro-5-(trifluoromethyl)-1,4-benzodiazepin-2-one;

7-Chloro-4-(2-fluoro-6-methoxybenzyl)-1,5-dihydro-5-(trifluoromethyl)-1,4-benzodiazepin-2-one;

7-Chloro-4-phenyl-5-butyl-1,5-dihydro-5-(trifluoromethyl)-1,4-benzodiazepin-2-one;

or a pharmaceutically acceptable salt form thereof.

24. The compound according to claim 1, wherein the compound is selected from the group:

7-Chloro-4-(2-pentynyl)-1,5-dihydro-5-(trifluoromethyl)-1,4-benzodiazepin-2-one;

7-Chloro-5-(cyclopropylethynyl)-1,5-dihydro-5-(trifluoromethyl)-1,4-benzodiazepin-2-one;

7-Chloro-4-phenyl-1,5-dihydro-5-(trifluoromethyl)-1,4-benzodiazepin-2-one;

7-Chloro-4-(2-propynyl)-1,5-dihydro-5-(trifluoromethyl)-1,4-benzodiazepin-2-one;

7-Chloro-4-(2-butynyl)-1,5-dihydro-5-(trifluoromethyl)-1,4-benzodiazepin-2-one;

or a pharmaceutically acceptable salt form thereof.

25. The compound according to claim 1, wherein the compound is selected from the group:

7-Chloro-5-(2-cyclopropyl-2-ethanonyl)-1,5-dihydro-5-(trifluoromethyl)-1,4-benzodiazepin-2-one;

7-Chloro-5-benzyl-1,5-dihydro-5-(trifluoromethyl)-1,4-benzodiazepin-2-one;

7-Chloro-5-(2-methylpropyl)-1,5-dihydro-5-(trifluoromethyl)-1,4-benzodiazepin-2-one;

7-Chloro-5-(2-phenylethyl)-1,5-dihydro-5-(trifluoromethyl)-1,4-benzodiazepin-2-one;

7-Chloro-3-methyl-5-(4-methylbutyl)-1,5-dihydro-5-(trifluoromethyl)-1,4-benzodiazepin-2-one;

or a pharmaceutically acceptable salt form thereof.

26. The compound according to claim 1, wherein the compound is selected from the group:

7-Chloro-3-methyl-5-(cyclopropylethynyl)-1,5-dihydro-5-(trifluoromethyl)-1,4-benzodiazepin-2-one;

7-Chloro-5-(cyclopropylethynyl)-1,5-dihydro-5-(trifluoromethyl)-1,4-benzodiazepin-2-one;

7-Chloro-5(S)-(cyclopropylethynyl)-1,5-dihydro-5-(trifluoromethyl)-1,4-benzodiazepin-2-one;

7-Chloro-4-methyl-5-(cyclopropylethynyl)-1,5-dihydro-5-(trifluoromethyl)-1,4-benzodiazepin-2-one;

7-Chloro-3-(2-methylpropyl)-5-pentyl-1,5-dihydro-5-(trifluoromethyl)-1,4-benzodiazepin-2-one;

or a pharmaceutically acceptable salt form thereof.

27. The compound according to claim 1, wherein the compound is selected from the group:

7-Chloro-3-methyl-5-(2-cyclopropylethynyl)-1,5-dihydro-5-(trifluoromethyl)-1,4-benzodiazepin-2-one;

7-Chloro-5-pentyl-1,5-dihydro-5-(trifluoromethyl)-1,4-benzodiazepin-2-one;

7-Chloro-4-(2-fluoro-6-methylbenzyl)-1,5-dihydro-5-(trifluoromethyl)-1,4-benzodiazepin-2-one;

3-Methyl-5-pentyl-1,5-dihydro-5-(trifluoromethyl)-1,4-benzodiazepin-2-one;

7-Chloro-3-methyl-5-(2-cyclopropylethynyl)-1,5-dihydro-5-(trifluoromethyl)-1,4-benzodiazepin-2-one;

or a pharmaceutically acceptable salt form thereof.

28. The compound according to claim 1, wherein the compound is selected from the group:

3(R)-Methyl-5-(2-cyclopropylethynyl)-1,5-dihydro-5-(trifluoromethyl)-1,4-benzodiazepin-2-one;

3(S)-Methyl-5-(cyclopropylethynyl)-1,5-dihydro-5-(trifluoromethyl)-1,4-benzodiazepin-2-one;

3-Ethyl-5-(cyclopropylethynyl)-1,5-dihydro-5-(trifluoromethyl)-1,4-benzodiazepin-2-one;

7-Chloro-5-pentyl-1,5-dihydro-5-(trifluoromethyl)-1,4-benzodiazepin-2-one;

7-Chloro-5-(3-methylbutyl)-1,5-dihydro-5-(trifluoromethyl)-1,4-benzodiazepin-2-one;

or a pharmaceutically acceptable salt form thereof.

29. The compound according to claim 1, wherein the compound is selected from the group:

7-Chloro-5-benzyl-1,5-dihydro-5-(trifluoromethyl)-1,4-benzodiazepin-2-one;

7-Chloro-5-(2-cyclopropyl-E-ethenyl)-1,5-dihydro-5-(trifluoromethyl)-1,4-benzodiazepin-2-one;

7-Chloro-5-hexyl-1,5-dihydro-5-(trifluoromethyl)-1,4-benzodiazepin-2-one;

7-Chloro-5-(2-cyclopropylethyl)-1,5-dihydro-5-(trifluoromethyl)-1,4-benzodiazepin-2-one;

7-Chloro-3-methyl-5-(2-cyclopropylethyl)-1,5-dihydro-5-(trifluoromethyl)-1,4-benzodiazepin-2-one;

or a pharmaceutically acceptable salt form thereof.

30. The compound according to claim 1, wherein the compound is selected from the group:

6,7-Difluoro-5-(2-cyclopropylethynyl)-1,5-dihydro-5-(trifluoromethyl)-1,4-benzodiazepin-2-one;

7-Chloro-5-(cyclopropylmethyl)-1,5-dihydro-5-(trifluoromethyl)-1,4-benzodiazepin-2-one;

7-Chloro-5-(4,4,4-trifluorobutyl)-1,5-dihydro-5-(trifluoromethyl)-1,4-benzodiazepin-2-one;

7-Methoxy-5-(cyclopropylethynyl)-1,5-dihydro-5-(trifluoromethyl)-1,4-benzodiazepin-2-one;

7-Fluoro-5-(cyclopropylethynyl)-1,5-dihydro-5-(trifluoromethyl)-1,4-benzodiazepin-2-one;

or a pharmaceutically acceptable salt form thereof.

31. The compound according to claim 1, wherein the compound is selected from the group:

7-Fluoro-5-(2-cyclopropyl-Z-ethenyl)-1,5-dihydro-5-(trifluoromethyl)-1,4-benzodiazepin-2-one;

6,7-Difluoro-5-(3,3,3-trifluoropropyl)-1,5-dihydro-5-(trifluoromethyl)-1,4-benzodiazepin-2-one;

7-Chloro-5-(2-pyridylmethyl)-1,5-dihydro-5-(trifluoromethyl)-1,4-benzodiazepin-2-one;

7-Chloro-5-butyl-1,5-dihydro-5-(trifluoromethyl)-1,4-benzodiazepin-2-one;

or a pharmaceutically acceptable salt form thereof.

32. A pharmaceutical composition, comprising: a pharmaceutically acceptable carrier and a therapeutically effective amount of a compound of claim 4 or pharmaceutically acceptable salt form thereof.

33. A method for treating HIV infection, comprising: administering to a host in need of such treatment a therapeutically effective amount of a compound of claim 4 or pharmaceutically acceptable salt form thereof.

* * * * *